US008328065B2

(12) United States Patent
Shah

(10) Patent No.: US 8,328,065 B2
(45) Date of Patent: Dec. 11, 2012

(54) KNIFE/FIRING ROD CONNECTION FOR SURGICAL INSTRUMENT

(75) Inventor: Sachin Shah, Milford, CT (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 13/292,270

(22) Filed: Nov. 9, 2011

(65) Prior Publication Data

US 2012/0048911 A1 Mar. 1, 2012

Related U.S. Application Data

(63) Continuation of application No. 12/780,431, filed on May 14, 2010, now Pat. No. 8,074,862, which is a continuation of application No. 12/134,351, filed on Jun. 6, 2008, now Pat. No. 7,789,283.

(51) Int. Cl.
*A61B 17/00* (2006.01)
(52) U.S. Cl. ............ 227/180.1; 227/175.1; 227/175.4
(58) Field of Classification Search ........... 227/175.1, 227/175.2, 175.4, 180.1, 181.1
See application file for complete search history.

(56) References Cited

U.S. PATENT DOCUMENTS

| | | | |
|---|---|---|---|
| 3,079,606 A | 3/1963 | Bobrov et al. |
| 3,490,675 A | 1/1970 | Green et al. |
| 3,777,538 A | 12/1973 | Weatherly et al. |
| 3,882,854 A | 5/1975 | Hulka et al. |
| 4,027,510 A | 6/1977 | Hiltebrandt |
| 4,086,926 A | 5/1978 | Green et al. |
| 4,244,372 A | 1/1981 | Kapitanov et al. |
| 4,429,695 A | 2/1984 | Green |
| 4,505,414 A | 3/1985 | Filipi |
| 4,520,817 A | 6/1985 | Green |
| 4,589,413 A | 5/1986 | Malyshev et al. |
| 4,596,351 A | 6/1986 | Fedotov et al. |
| 4,602,634 A | 7/1986 | Barkley |
| 4,605,001 A | 8/1986 | Rothfuss et al. |
| 4,608,981 A | 9/1986 | Rothfuss et al. |
| 4,610,383 A | 9/1986 | Rothfuss et al. |
| 4,633,861 A | 1/1987 | Chow et al. |
| 4,633,874 A | 1/1987 | Chow et al. |
| 4,671,445 A | 6/1987 | Barker et al. |

(Continued)

FOREIGN PATENT DOCUMENTS

AU 5476586 9/1986

(Continued)

OTHER PUBLICATIONS

European Search Report for EP 09251399.3 2310 date of completion is Sep. 7, 2009 (3 pages).

(Continued)

*Primary Examiner* — Paul R Durand

(57) ABSTRACT

A surgical instrument including a frame, an elongate portion, a firing rod and an end effector is disclosed. The elongate portion extends distally from the frame and defines a longitudinal axis. The firing rod is disposed at least partially with the elongate portion and is proximally and distally translatable with respect to the elongate portion. The end effector includes a knife and is disposed at a distal portion of the elongate portion. Distal movement of the firing rod causes a distal end of the firing rod to link with the knife. Proximal movement of the firing rod moves the linked knife proximally to a first predetermined position. The knife is unlinked from the firing rod when the firing rod has been translated proximally to a second predetermined position.

9 Claims, 11 Drawing Sheets

U.S. PATENT DOCUMENTS

| | | | |
|---|---|---|---|
| 4,700,703 A | 10/1987 | Resnick et al. | |
| 4,703,887 A | 11/1987 | Clanton et al. | |
| 4,728,020 A | 3/1988 | Green et al. | |
| 4,752,024 A | 6/1988 | Green et al. | |
| 4,784,137 A | 11/1988 | Kulik et al. | |
| 4,863,088 A | 9/1989 | Redmond et al. | |
| 4,869,415 A | 9/1989 | Fox et al. | |
| 4,892,244 A | 1/1990 | Fox et al. | |
| 4,955,959 A | 9/1990 | Tompkins et al. | |
| 4,978,049 A | 12/1990 | Green | |
| 4,991,764 A | 2/1991 | Mericle | |
| 5,014,899 A | 5/1991 | Presty | |
| 5,031,814 A * | 7/1991 | Tompkins et al. | 227/8 |
| 5,040,715 A | 8/1991 | Green et al. | |
| 5,065,929 A | 11/1991 | Schulze et al. | |
| 5,071,430 A | 12/1991 | de Salis et al. | |
| 5,074,454 A | 12/1991 | Peters | |
| 5,083,695 A | 1/1992 | Foslien et al. | |
| 5,084,057 A | 1/1992 | Green et al. | |
| 5,106,008 A | 4/1992 | Tompkins | |
| 5,111,987 A | 5/1992 | Moeinzadeh et al. | |
| 5,129,570 A | 7/1992 | Schulze et al. | |
| 5,141,144 A | 8/1992 | Foslien et al. | |
| 5,156,315 A | 10/1992 | Green et al. | |
| 5,156,614 A | 10/1992 | Green et al. | |
| 5,163,943 A | 11/1992 | Mohiuddin et al. | |
| 5,170,925 A | 12/1992 | Madden et al. | |
| 5,171,247 A | 12/1992 | Hughett et al. | |
| 5,173,133 A | 12/1992 | Morin et al. | |
| 5,180,092 A | 1/1993 | Crainich | |
| 5,188,274 A | 2/1993 | Moeinzadeh et al. | |
| 5,220,928 A | 6/1993 | Oddsen et al. | |
| 5,221,036 A | 6/1993 | Takase et al. | |
| 5,242,457 A | 9/1993 | Akopov et al. | |
| 5,246,156 A | 9/1993 | Rothfuss et al. | |
| 5,253,793 A | 10/1993 | Green et al. | |
| 5,263,629 A | 11/1993 | Trumbull et al. | |
| RE34,519 E | 1/1994 | Fox et al. | |
| 5,275,323 A | 1/1994 | Schulze et al. | |
| 5,282,807 A | 2/1994 | Knoepfler | |
| 5,289,963 A | 3/1994 | McGarry et al. | |
| 5,307,976 A | 5/1994 | Olson et al. | |
| 5,308,576 A | 5/1994 | Green et al. | |
| 5,312,023 A | 5/1994 | Green et al. | |
| 5,318,221 A | 6/1994 | Green et al. | |
| 5,326,013 A | 7/1994 | Green et al. | |
| 5,328,077 A | 7/1994 | Lou | |
| 5,330,486 A | 7/1994 | Wilk | |
| 5,332,142 A | 7/1994 | Robinson et al. | |
| 5,336,232 A | 8/1994 | Green et al. | |
| 5,344,061 A | 9/1994 | Crainich | |
| 5,352,238 A | 10/1994 | Green et al. | |
| 5,356,064 A | 10/1994 | Green et al. | |
| 5,358,506 A | 10/1994 | Green et al. | |
| 5,364,001 A | 11/1994 | Bryan | |
| 5,364,002 A | 11/1994 | Green et al. | |
| 5,364,003 A | 11/1994 | Williamson, IV | |
| 5,366,133 A | 11/1994 | Geiste | |
| 5,376,095 A | 12/1994 | Ortiz | |
| 5,379,933 A | 1/1995 | Green et al. | |
| 5,381,943 A | 1/1995 | Allen et al. | |
| 5,382,255 A | 1/1995 | Castro et al. | |
| 5,383,880 A | 1/1995 | Hooven | |
| 5,395,033 A | 3/1995 | Byrne et al. | |
| 5,395,034 A | 3/1995 | Allen et al. | |
| 5,397,046 A | 3/1995 | Savage et al. | |
| 5,397,324 A | 3/1995 | Carroll et al. | |
| 5,405,072 A | 4/1995 | Zlock et al. | |
| 5,407,293 A | 4/1995 | Crainich | |
| 5,413,268 A | 5/1995 | Green et al. | |
| 5,415,334 A | 5/1995 | Williamson, IV et al. | |
| 5,415,335 A | 5/1995 | Knodell, Jr. | |
| 5,417,361 A | 5/1995 | Williamson, IV | |
| 5,423,471 A | 6/1995 | Mastri et al. | |
| 5,425,745 A | 6/1995 | Green et al. | |
| 5,431,322 A | 7/1995 | Green et al. | |
| 5,431,323 A | 7/1995 | Smith et al. | |
| 5,433,721 A | 7/1995 | Hooven et al. | |
| 5,441,193 A | 8/1995 | Gravener | |
| 5,445,304 A | 8/1995 | Plyley et al. | |
| 5,447,265 A | 9/1995 | Vidal et al. | |
| 5,452,837 A | 9/1995 | Williamson, IV et al. | |
| 5,456,401 A | 10/1995 | Green et al. | |
| 5,464,300 A | 11/1995 | Crainich | |
| 5,465,895 A | 11/1995 | Knodel et al. | |
| 5,467,911 A | 11/1995 | Tsuruta et al. | |
| 5,470,007 A | 11/1995 | Plyley et al. | |
| 5,470,010 A | 11/1995 | Rothfuss et al. | |
| 5,472,132 A | 12/1995 | Savage et al. | |
| 5,474,566 A | 12/1995 | Alesi et al. | |
| 5,476,206 A | 12/1995 | Green et al. | |
| 5,478,003 A | 12/1995 | Green et al. | |
| 5,480,089 A | 1/1996 | Blewett | |
| 5,482,197 A | 1/1996 | Green et al. | |
| 5,484,095 A | 1/1996 | Green et al. | |
| 5,484,451 A | 1/1996 | Akopov et al. | |
| 5,485,947 A | 1/1996 | Olson et al. | |
| 5,485,952 A | 1/1996 | Fontayne | |
| 5,486,185 A | 1/1996 | Freitas et al. | |
| 5,487,499 A | 1/1996 | Sorrentino et al. | |
| 5,487,500 A | 1/1996 | Knodel et al. | |
| 5,489,058 A | 2/1996 | Plyley et al. | |
| 5,490,856 A | 2/1996 | Person et al. | |
| 5,497,933 A | 3/1996 | DeFonzo et al. | |
| 5,501,689 A | 3/1996 | Green et al. | |
| 5,505,363 A | 4/1996 | Green et al. | |
| 5,507,426 A | 4/1996 | Young et al. | |
| 5,518,163 A | 5/1996 | Hooven | |
| 5,518,164 A | 5/1996 | Hooven | |
| 5,529,235 A | 6/1996 | Boiarski et al. | |
| 5,531,744 A | 7/1996 | Nardella et al. | |
| 5,535,934 A | 7/1996 | Boiarski et al. | |
| 5,535,935 A | 7/1996 | Vidal et al. | |
| 5,535,937 A | 7/1996 | Boiarski et al. | |
| 5,540,375 A | 7/1996 | Bolanos et al. | |
| 5,542,594 A | 8/1996 | McKean et al. | |
| 5,549,628 A | 8/1996 | Cooper et al. | |
| 5,551,622 A | 9/1996 | Yoon | |
| 5,553,765 A | 9/1996 | Knodel et al. | |
| 5,554,164 A | 9/1996 | Wilson et al. | |
| 5,554,169 A | 9/1996 | Green et al. | |
| 5,560,530 A | 10/1996 | Bolanos et al. | |
| 5,560,532 A | 10/1996 | DeFonzo et al. | |
| 5,562,239 A | 10/1996 | Boiarski et al. | |
| 5,562,241 A | 10/1996 | Knodel et al. | |
| 5,562,682 A | 10/1996 | Oberlin et al. | |
| 5,562,701 A | 10/1996 | Huitema et al. | |
| 5,564,615 A | 10/1996 | Bishop et al. | |
| 5,571,116 A | 11/1996 | Bolanos et al. | |
| 5,573,169 A | 11/1996 | Green et al. | |
| 5,573,543 A | 11/1996 | Akopov et al. | |
| 5,575,799 A | 11/1996 | Bolanos et al. | |
| 5,575,803 A | 11/1996 | Cooper et al. | |
| 5,577,654 A | 11/1996 | Bishop | |
| 5,579,107 A | 11/1996 | Wright et al. | |
| 5,584,425 A | 12/1996 | Savage et al. | |
| 5,586,711 A | 12/1996 | Plyley et al. | |
| 5,588,580 A | 12/1996 | Paul et al. | |
| 5,588,581 A | 12/1996 | Conlon et al. | |
| 5,597,107 A | 1/1997 | Knodel et al. | |
| 5,601,224 A | 2/1997 | Bishop et al. | |
| 5,607,095 A | 3/1997 | Smith et al. | |
| 5,615,820 A | 4/1997 | Viola | |
| 5,618,291 A | 4/1997 | Thompson et al. | |
| 5,624,452 A | 4/1997 | Yates | |
| 5,626,587 A | 5/1997 | Bishop et al. | |
| 5,628,446 A | 5/1997 | Geiste et al. | |
| 5,630,539 A | 5/1997 | Plyley et al. | |
| 5,630,540 A | 5/1997 | Blewett | |
| 5,630,541 A | 5/1997 | Williamson et al. | |
| 5,632,432 A | 5/1997 | Schulze et al. | |
| 5,634,584 A | 6/1997 | Okorocha et al. | |
| 5,636,780 A | 6/1997 | Green et al. | |
| 5,645,209 A | 7/1997 | Green et al. | |
| 5,647,526 A | 7/1997 | Green et al. | |
| 5,651,491 A | 7/1997 | Heaton et al. | |
| 5,653,373 A | 8/1997 | Green et al. | |

| | | | | | | |
|---|---|---|---|---|---|---|
| 5,653,374 | A | 8/1997 | Young et al. | 5,919,198 A | 7/1999 | Graves, Jr. et al. |
| 5,653,721 | A | 8/1997 | Knodel et al. | 5,922,001 A | 7/1999 | Yoon |
| 5,655,698 | A | 8/1997 | Yoon | 5,931,847 A | 8/1999 | Bittner et al. |
| 5,657,921 | A | 8/1997 | Young et al. | 5,941,442 A | 8/1999 | Geiste et al. |
| 5,658,300 | A | 8/1997 | Bito et al. | 5,954,259 A | 9/1999 | Viola et al. |
| 5,662,258 | A | 9/1997 | Knodel et al. | 5,980,510 A | 11/1999 | Tsonton et al. |
| 5,662,259 | A | 9/1997 | Yoon | 5,988,479 A | 11/1999 | Palmer |
| 5,662,260 | A | 9/1997 | Yoon | 6,004,335 A | 12/1999 | Vaitekunas et al. |
| 5,662,662 | A | 9/1997 | Bishop et al. | 6,010,054 A | 1/2000 | Johnson et al. |
| 5,662,666 | A | 9/1997 | Onuki et al. | 6,032,849 A | 3/2000 | Mastri et al. |
| 5,665,085 | A | 9/1997 | Nardella | 6,045,560 A | 4/2000 | McKean et al. |
| 5,667,517 | A | 9/1997 | Hooven | 6,063,097 A | 5/2000 | Oi et al. |
| 5,669,544 | A | 9/1997 | Schulze et al. | 6,079,606 A | 6/2000 | Milliman et al. |
| 5,673,840 | A | 10/1997 | Schulze et al. | 6,099,551 A | 8/2000 | Gabbay |
| 5,673,841 | A | 10/1997 | Schulze et al. | 6,109,500 A | 8/2000 | Alli et al. |
| 5,673,842 | A | 10/1997 | Bittner et al. | 6,131,789 A | 10/2000 | Schulze et al. |
| 5,676,674 | A | 10/1997 | Botanos et al. | 6,131,790 A | 10/2000 | Piraka |
| 5,680,981 | A | 10/1997 | Mililli et al. | 6,155,473 A | 12/2000 | Tompkins et al. |
| 5,680,982 | A | 10/1997 | Schulze et al. | 6,197,017 B1 | 3/2001 | Brock et al. |
| 5,690,269 | A | 11/1997 | Bolanos et al. | 6,202,914 B1 | 3/2001 | Geiste et al. |
| 5,692,668 | A | 12/1997 | Schulze et al. | 6,241,139 B1 | 6/2001 | Milliman et al. |
| 5,697,542 | A | 12/1997 | Knodel et al. | 6,250,532 B1 | 6/2001 | Green et al. |
| 5,702,409 | A | 12/1997 | Rayburn et al. | 6,264,086 B1 | 7/2001 | McGuckin, Jr. |
| 5,704,534 | A | 1/1998 | Huitema et al. | 6,264,087 B1 | 7/2001 | Whitman |
| 5,706,997 | A | 1/1998 | Green et al. | 6,269,977 B1 | 8/2001 | Moore |
| 5,709,334 | A | 1/1998 | Sorrentino et al. | 6,279,809 B1 | 8/2001 | Nicolo |
| 5,711,472 | A | 1/1998 | Bryan | 6,315,183 B1 | 11/2001 | Piraka |
| 5,713,505 | A | 2/1998 | Huitema | 6,315,184 B1 | 11/2001 | Whitman |
| 5,715,988 | A | 2/1998 | Palmer | 6,325,810 B1 | 12/2001 | Hamilton et al. |
| 5,716,366 | A | 2/1998 | Yates | 6,330,965 B1 * | 12/2001 | Milliman et al. .......... 227/176.1 |
| 5,718,359 | A | 2/1998 | Palmer et al. | 6,391,038 B2 | 5/2002 | Vargas et al. |
| 5,725,536 | A | 3/1998 | Oberlin et al. | 6,398,797 B2 | 6/2002 | Bombard et al. |
| 5,725,554 | A | 3/1998 | Simon et al. | 6,436,097 B1 | 8/2002 | Nardella |
| 5,728,110 | A | 3/1998 | Vidal et al. | 6,439,446 B1 | 8/2002 | Perry et al. |
| 5,732,806 | A | 3/1998 | Foshee et al. | 6,443,973 B1 | 9/2002 | Whitman |
| 5,735,848 | A | 4/1998 | Yates et al. | 6,463,623 B2 | 10/2002 | Ahn et al. |
| 5,743,456 | A | 4/1998 | Jones et al. | 6,478,804 B2 | 11/2002 | Vargas et al. |
| 5,749,893 | A * | 5/1998 | Vidal et al. .................... 606/205 | 6,488,196 B1 | 12/2002 | Fenton, Jr. |
| 5,752,644 | A | 5/1998 | Bolanos et al. | 6,503,257 B2 | 1/2003 | Grant et al. |
| 5,762,255 | A | 6/1998 | Chrisman et al. | 6,505,768 B2 | 1/2003 | Whitman |
| 5,762,256 | A | 6/1998 | Mastri et al. | 6,544,274 B2 | 4/2003 | Danitz et al. |
| 5,769,303 | A | 6/1998 | Knodel et al. | 6,554,844 B2 | 4/2003 | Lee et al. |
| 5,769,892 | A | 6/1998 | Kingwell | 6,565,554 B1 | 5/2003 | Niemeyer |
| 5,772,099 | A | 6/1998 | Gravener | 6,587,750 B2 | 7/2003 | Gerbi et al. |
| 5,772,673 | A | 6/1998 | Cuny et al. | 6,592,597 B2 | 7/2003 | Grant et al. |
| 5,779,130 | A | 7/1998 | Alesi et al. | 6,594,552 B1 | 7/2003 | Nowlin et al. |
| 5,779,131 | A | 7/1998 | Knodel et al. | 6,602,252 B2 | 8/2003 | Mollenauer |
| 5,779,132 | A | 7/1998 | Knodel et al. | 6,612,053 B2 | 9/2003 | Liao |
| 5,782,396 | A | 7/1998 | Mastri et al. | 6,619,529 B2 | 9/2003 | Green et al. |
| 5,782,397 | A | 7/1998 | Koukline | 6,644,532 B2 | 11/2003 | Green et al. |
| 5,782,834 | A | 7/1998 | Lucey et al. | 6,656,193 B2 | 12/2003 | Grant et al. |
| 5,785,232 | A | 7/1998 | Vidal et al. | 6,669,073 B2 | 12/2003 | Milliman et al. |
| 5,797,536 | A | 8/1998 | Smith et al. | 6,681,978 B2 | 1/2004 | Geiste et al. |
| 5,797,537 | A | 8/1998 | Oberlin et al. | 6,698,643 B2 | 3/2004 | Whitman |
| 5,797,538 | A | 8/1998 | Heaton et al. | 6,716,232 B1 | 4/2004 | Vidal et al. |
| 5,810,811 | A | 9/1998 | Yates et al. | 6,722,552 B2 | 4/2004 | Fenton, Jr. |
| 5,810,855 | A | 9/1998 | Rayburn et al. | 6,731,473 B2 | 5/2004 | Li et al. |
| 5,814,055 | A | 9/1998 | Knodel et al. | 6,755,338 B2 | 6/2004 | Hahnen et al. |
| 5,814,057 | A | 9/1998 | Oi et al. | 6,783,524 B2 | 8/2004 | Anderson et al. |
| 5,816,471 | A | 10/1998 | Plyley et al. | 6,786,382 B1 | 9/2004 | Hoffman |
| 5,817,109 | A | 10/1998 | McGarry et al. | 6,808,262 B2 | 10/2004 | Chapoy et al. |
| 5,820,009 | A | 10/1998 | Melting et al. | 6,817,509 B2 | 11/2004 | Geiste et al. |
| 5,823,066 | A | 10/1998 | Huitema et al. | 6,830,174 B2 | 12/2004 | Hillstead et al. |
| 5,826,776 | A | 10/1998 | Schutze et al. | 6,835,199 B2 | 12/2004 | McGuckin, Jr. et al. |
| 5,829,662 | A | 11/1998 | Allen et al. | 6,843,403 B2 | 1/2005 | Whitman |
| 5,833,695 | A | 11/1998 | Yoon | RE38,708 E | 3/2005 | Bolanos et al. |
| 5,836,147 | A | 11/1998 | Schnipke | 6,877,647 B2 | 4/2005 | Green et al. |
| 5,862,972 | A | 1/1999 | Green et al. | 6,879,880 B2 | 4/2005 | Nowlin et al. |
| 5,865,361 | A | 2/1999 | Mitliman et al. | 6,889,116 B2 | 5/2005 | Jinno |
| 5,871,135 | A | 2/1999 | Williamson, IV et al. | 6,905,057 B2 | 6/2005 | Swayze et al. |
| 5,873,873 | A | 2/1999 | Smith et al. | 6,953,138 B1 | 10/2005 | Dworak et al. |
| 5,878,938 | A | 3/1999 | Bittner et al. | 6,953,139 B2 | 10/2005 | Mitliman et al. |
| 5,893,506 | A | 4/1999 | Powell | 6,959,852 B2 | 11/2005 | Shelton, IV et al. |
| 5,894,979 | A | 4/1999 | Powell | 6,962,594 B1 | 11/2005 | Thevenet |
| 5,897,562 | A | 4/1999 | Bolanos et al. | 6,964,363 B2 | 11/2005 | Wales et al. |
| 5,901,895 | A | 5/1999 | Heaton et al. | 6,978,921 B2 | 12/2005 | Shelton, IV et al. |
| 5,911,352 | A | 6/1999 | Racenet et al. | 6,981,628 B2 | 1/2006 | Wales |
| 5,911,353 | A | 6/1999 | Bolanos et al. | 6,986,451 B1 | 1/2006 | Mastri et al. |
| 5,918,791 | A | 7/1999 | Sorrentino et al. | 6,988,649 B2 | 1/2006 | Shelton, IV et al. |

| Patent No. | Date | Inventor |
|---|---|---|
| 6,991,627 B2 | 1/2006 | Madhani et al. |
| 6,994,714 B2 | 2/2006 | Vargas et al. |
| 7,000,818 B2 | 2/2006 | Shelton, IV et al. |
| 7,000,819 B2 | 2/2006 | Swayze et al. |
| 7,032,799 B2 | 4/2006 | Viola et al. |
| 7,044,352 B2 | 5/2006 | Shelton, IV et al. |
| 7,044,353 B2 | 5/2006 | Mastri et al. |
| 7,055,730 B2 | 6/2006 | Ehrenfels et al. |
| 7,055,731 B2 | 6/2006 | Shelton, IV et al. |
| 7,059,508 B2 | 6/2006 | Shelton, IV et al. |
| 7,070,083 B2 | 7/2006 | Jankowski |
| 7,083,075 B2 | 8/2006 | Swayze et al. |
| 7,097,089 B2 | 8/2006 | Marczyk |
| 7,111,769 B2 | 9/2006 | Wales et al. |
| 7,114,642 B2 | 10/2006 | Whitman |
| 7,121,446 B2 | 10/2006 | Arad et al. |
| 7,128,253 B2 | 10/2006 | Mastri et al. |
| 7,128,254 B2 | 10/2006 | Shelton, IV et al. |
| 7,140,527 B2 | 11/2006 | Ehrenfels et al. |
| 7,140,528 B2 | 11/2006 | Shelton, IV |
| 7,143,923 B2 | 12/2006 | Shelton, IV et al. |
| 7,143,924 B2 | 12/2006 | Scirica et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,159,750 B2 | 1/2007 | Racenet et al. |
| 7,172,104 B2 | 2/2007 | Scirica et al. |
| 7,188,758 B2 | 3/2007 | Viola et al. |
| 7,207,471 B2 | 4/2007 | Heinrich et al. |
| 7,213,736 B2 | 5/2007 | Wales et al. |
| 7,225,963 B2 | 6/2007 | Scirica et al. |
| 7,225,964 B2 | 6/2007 | Mastri et al. |
| 7,238,195 B2 | 7/2007 | Viola |
| 7,246,734 B2 | 7/2007 | Shelton, IV |
| 7,258,262 B2 | 8/2007 | Mastri et al. |
| 7,278,562 B2 | 10/2007 | Mastri et al. |
| 7,278,563 B1 | 10/2007 | Green |
| 7,287,682 B1 | 10/2007 | Ezzat et al. |
| 7,293,685 B2 | 11/2007 | Ehrenfels et al. |
| 7,296,724 B2 | 11/2007 | Green et al. |
| 7,296,772 B2 | 11/2007 | Wang |
| 7,300,444 B1 | 11/2007 | Nielsen et al. |
| 7,303,108 B2 | 12/2007 | Shelton, IV |
| 7,308,998 B2 * | 12/2007 | Mastri et al. ............... 227/176.1 |
| 7,328,828 B2 | 2/2008 | Ortiz et al. |
| 7,328,829 B2 | 2/2008 | Arad et al. |
| 7,354,447 B2 | 4/2008 | Shelton, IV et al. |
| 7,357,287 B2 | 4/2008 | Shelton, IV et al. |
| 7,364,061 B2 | 4/2008 | Swayze et al. |
| 7,367,485 B2 | 5/2008 | Shelton, IV et al. |
| 7,380,695 B2 | 6/2008 | Doll et al. |
| 7,380,696 B2 | 6/2008 | Shelton, IV et al. |
| 7,399,310 B2 | 7/2008 | Edoga et al. |
| 7,401,720 B1 | 7/2008 | Durraril |
| 7,404,508 B2 | 7/2008 | Smith et al. |
| 7,404,509 B2 | 7/2008 | Ortiz et al. |
| 7,407,074 B2 | 8/2008 | Ortiz et al. |
| 7,407,077 B2 | 8/2008 | Ortiz et al. |
| 7,407,078 B2 | 8/2008 | Shelton, IV et al. |
| 7,416,101 B2 | 8/2008 | Shelton, IV et al. |
| 7,419,080 B2 | 9/2008 | Smith et al. |
| 7,419,495 B2 | 9/2008 | Menn et al. |
| 7,422,139 B2 | 9/2008 | Shelton, IV et al. |
| 7,431,189 B2 | 10/2008 | Shelton, IV et al. |
| 7,434,715 B2 | 10/2008 | Shelton, IV et al. |
| 7,434,717 B2 | 10/2008 | Shelton, IV et al. |
| 7,438,208 B2 | 10/2008 | Larson |
| 7,438,209 B1 | 10/2008 | Hess et al. |
| 7,441,684 B2 | 10/2008 | Shelton, IV et al. |
| 7,441,685 B1 | 10/2008 | Boudreaux |
| 7,448,525 B2 | 11/2008 | Shelton, IV et al. |
| 7,451,904 B2 | 11/2008 | Shelton, IV |
| 7,455,208 B2 | 11/2008 | Wales et al. |
| 7,458,494 B2 | 12/2008 | Matsutani et al. |
| 7,461,767 B2 | 12/2008 | Viola et al. |
| 7,462,185 B1 | 12/2008 | Knodél |
| 7,464,846 B2 | 12/2008 | Shelton, IV et al. |
| 7,464,848 B2 | 12/2008 | Green et al. |
| 7,464,849 B2 | 12/2008 | Shelton, IV et al. |
| 7,467,740 B2 | 12/2008 | Shelton, IV et al. |
| 7,472,814 B2 | 1/2009 | Mastri et al. |
| 7,472,815 B2 | 1/2009 | Shelton, IV et al. |
| 7,472,816 B2 | 1/2009 | Holsten et al. |
| 7,473,258 B2 | 1/2009 | Clauson et al. |
| 7,481,347 B2 | 1/2009 | Roy |
| 7,481,348 B2 | 1/2009 | Marczyk |
| 7,481,349 B2 | 1/2009 | Holsten et al. |
| 7,487,899 B2 | 2/2009 | Shelton, IV et al. |
| 7,490,749 B2 | 2/2009 | Schall et al. |
| 7,494,039 B2 | 2/2009 | Racenet et al. |
| 7,500,979 B2 | 3/2009 | Hueil et al. |
| 7,503,474 B2 | 3/2009 | Hillstead et al. |
| 7,506,790 B2 | 3/2009 | Shelton, IV |
| 7,510,107 B2 | 3/2009 | Timm et al. |
| 7,513,408 B2 | 4/2009 | Shelton, IV et al. |
| 7,517,356 B2 | 4/2009 | Heinrich |
| 7,537,602 B2 | 5/2009 | Whitman |
| 7,543,729 B2 | 6/2009 | Ivanko |
| 7,543,730 B1 | 6/2009 | Marczyk |
| 7,543,731 B2 | 6/2009 | Green et al. |
| 7,556,185 B2 | 7/2009 | Viola |
| 7,556,186 B2 | 7/2009 | Milliman |
| 7,559,450 B2 | 7/2009 | Wales et al. |
| 7,559,452 B2 | 7/2009 | Wales et al. |
| 7,559,453 B2 | 7/2009 | Heinrch et al. |
| 7,559,937 B2 | 7/2009 | de la Torre et al. |
| 7,565,993 B2 | 7/2009 | Milliman et al. |
| 7,568,603 B2 | 8/2009 | Shelton, IV et al. |
| 7,568,604 B2 | 8/2009 | Ehrentels et al. |
| 7,571,845 B2 | 8/2009 | Viola |
| 7,575,144 B2 | 8/2009 | Ortiz et al. |
| 7,584,880 B2 | 9/2009 | Racenet et al. |
| 7,588,175 B2 | 9/2009 | Timm et al. |
| 7,588,176 B2 | 9/2009 | Timm et al. |
| 7,588,177 B2 | 9/2009 | Racenet |
| 7,597,229 B2 | 10/2009 | Boudreaux et al. |
| 7,597,230 B2 | 10/2009 | Racenet et al. |
| 7,604,150 B2 | 10/2009 | Boudreaux |
| 7,604,151 B2 | 10/2009 | Hess et al. |
| 7,607,557 B2 | 10/2009 | Shelton, IV et al. |
| 7,611,038 B2 | 11/2009 | Racenet et al. |
| 7,617,961 B2 | 11/2009 | Viola |
| 7,624,902 B2 | 12/2009 | Marczyk et al. |
| 7,624,903 B2 | 12/2009 | Green et al. |
| 7,631,793 B2 | 12/2009 | Rethy et al. |
| 7,631,794 B2 | 12/2009 | Rethy et al. |
| 7,635,073 B2 | 12/2009 | Heiririch |
| 7,635,074 B2 | 12/2009 | Olson et al. |
| 7,635,373 B2 | 12/2009 | Ortiz |
| 7,637,409 B2 | 12/2009 | Marczyk |
| 7,637,410 B2 | 12/2009 | Marczyk |
| 7,641,091 B2 | 1/2010 | Olson et al. |
| 7,641,093 B2 | 1/2010 | Doll et al. |
| 7,641,095 B2 | 1/2010 | Viola |
| 7,644,848 B2 | 1/2010 | Swayze et al. |
| 7,648,055 B2 | 1/2010 | Marczyk |
| 2002/0004498 A1 | 1/2002 | Doherty |
| 2002/0009193 A1 | 1/2002 | Deguchi |
| 2002/0018323 A1 | 2/2002 | Li |
| 2002/0032948 A1 | 3/2002 | Ahn |
| 2002/0036748 A1 | 3/2002 | Chapoy |
| 2002/0045442 A1 | 4/2002 | Silen et al. |
| 2002/0069595 A1 | 6/2002 | Knudson et al. |
| 2002/0084304 A1 | 7/2002 | Whitman |
| 2002/0111621 A1 | 8/2002 | Wallace et al. |
| 2002/0143346 A1 | 10/2002 | McGuckin, Jr. et al. |
| 2002/0177843 A1 | 11/2002 | Anderson et al. |
| 2002/0188294 A1 | 12/2002 | Couture et al. |
| 2002/0190093 A1 | 12/2002 | Fenton, Jr. |
| 2003/0009193 A1 | 1/2003 | Corsaro |
| 2003/0105476 A1 | 6/2003 | Sancoff et al. |
| 2003/0132268 A1 | 7/2003 | Whitman |
| 2004/0004105 A1 | 1/2004 | Jankowski |
| 2004/0007608 A1 | 1/2004 | Ehrenfels et al. |
| 2004/0050902 A1 | 3/2004 | Green et al. |
| 2004/0093029 A1 | 5/2004 | Zubik et al. |
| 2004/0094597 A1 | 5/2004 | Whitman |
| 2004/0108357 A1 | 6/2004 | Milliman |

| | | | | | |
|---|---|---|---|---|---|
| 2004/0149802 A1 | 8/2004 | Whitman | 2007/0034670 A1 | 2/2007 | Racenet et al. |
| 2004/0173659 A1 | 9/2004 | Green | 2007/0045379 A1 | 3/2007 | Shelton, IV |
| 2004/0199180 A1 | 10/2004 | Knodel et al. | 2007/0045380 A1 | 3/2007 | Mastri et al. |
| 2004/0199181 A1 | 10/2004 | Knodel et al. | 2007/0068989 A1 | 3/2007 | Shelton |
| 2004/0232199 A1 | 11/2004 | Shelton, IV et al. | 2007/0068990 A1 | 3/2007 | Shelton, IV et al. |
| 2004/0232200 A1 | 11/2004 | Shelton, IV et al. | 2007/0073340 A1 | 3/2007 | Shelton, IV et al. |
| 2004/0232201 A1 | 11/2004 | Wenchell | 2007/0073341 A1 | 3/2007 | Smith et al. |
| 2004/0243151 A1 | 12/2004 | Demmy | 2007/0075114 A1 | 4/2007 | Shelton, IV et al. |
| 2004/0267310 A1 | 12/2004 | Racenet | 2007/0075115 A1 | 4/2007 | Olson et al. |
| 2004/0267311 A1 | 12/2004 | Viola et al. | 2007/0075116 A1 | 4/2007 | Whitman |
| 2005/0006429 A1 | 1/2005 | Wales | 2007/0083233 A1 | 4/2007 | Ortiz et al. |
| 2005/0006430 A1 | 1/2005 | Wales | 2007/0083234 A1 | 4/2007 | Shelton, IV et al. |
| 2005/0006431 A1 | 1/2005 | Shelton, IV et al. | 2007/0084896 A1 | 4/2007 | Doll et al. |
| 2005/0006432 A1 | 1/2005 | Racenet | 2007/0084897 A1 | 4/2007 | Shelton, IV et al. |
| 2005/0006433 A1 | 1/2005 | Milliman | 2007/0084898 A1 | 4/2007 | Scirica |
| 2005/0006434 A1 | 1/2005 | Wales et al. | 2007/0084899 A1 | 4/2007 | Taylor |
| 2005/0023324 A1 | 2/2005 | Doll et al. | 2007/0102472 A1 | 5/2007 | Shelton, IV |
| 2005/0023325 A1 | 2/2005 | Gresham | 2007/0102473 A1 | 5/2007 | Shelton, IV |
| 2005/0067457 A1 | 3/2005 | Shelton | 2007/0102474 A1 | 5/2007 | Shelton, IV |
| 2005/0067458 A1 | 3/2005 | Swayze et al. | 2007/0102475 A1 | 5/2007 | Ortiz et al. |
| 2005/0067459 A1 | 3/2005 | Swayze et al. | 2007/0102476 A1 | 5/2007 | Shelton, IV |
| 2005/0067460 A1 | 3/2005 | Milliman | 2007/0106317 A1 | 5/2007 | Shelton, IV |
| 2005/0070925 A1 | 3/2005 | Shelton, IV et al. | 2007/0108252 A1 | 5/2007 | Racenet et al. |
| 2005/0070958 A1 | 3/2005 | Swayze et al. | 2007/0114261 A1 | 5/2007 | Ortiz et al. |
| 2005/0072827 A1 | 4/2005 | Mollenauer | 2007/0114262 A1 | 5/2007 | Mastri et al. |
| 2005/0082336 A1 | 4/2005 | Ivanko | 2007/0119900 A1 | 5/2007 | Ehrenfels et al. |
| 2005/0103819 A1 | 5/2005 | Racenet | 2007/0119901 A1 | 5/2007 | Ehrenfels et al. |
| 2005/0119669 A1 | 6/2005 | Demmy | 2007/0125826 A1 | 6/2007 | Shelton, IV |
| 2005/0127131 A1 | 6/2005 | Mastri | 2007/0125827 A1 | 6/2007 | Viola |
| 2005/0145671 A1 | 7/2005 | Viola | 2007/0125828 A1 | 6/2007 | Rethy |
| 2005/0159778 A1 | 7/2005 | Heinrich et al. | 2007/0145095 A1 | 6/2007 | Heinrich et al. |
| 2005/0165415 A1 | 7/2005 | Wales | 2007/0145096 A1 | 6/2007 | Viola et al. |
| 2005/0173490 A1 | 8/2005 | Shelton, IV | 2007/0152014 A1 | 7/2007 | Gillum et al. |
| 2005/0178813 A1 | 8/2005 | Swayze et al. | 2007/0158385 A1 | 7/2007 | Hueil et al. |
| 2005/0184121 A1 | 8/2005 | Heinrich | 2007/0170225 A1 | 7/2007 | Shelton, IV et al. |
| 2005/0184123 A1 | 8/2005 | Scirica et al. | 2007/0175947 A1 | 8/2007 | Ortiz et al. |
| 2005/0184124 A1 | 8/2005 | Scirica et al. | 2007/0175948 A1 | 8/2007 | Scirica et al. |
| 2005/0184125 A1 | 8/2005 | Marczyk | 2007/0175949 A1 | 8/2007 | Shelton, IV et al. |
| 2005/0184126 A1 | 8/2005 | Green et al. | 2007/0175950 A1 | 8/2007 | Shelton, IV et al. |
| 2005/0189397 A1 | 9/2005 | Jankowski | 2007/0175951 A1 | 8/2007 | Shelton, IV et al. |
| 2005/0192628 A1 | 9/2005 | Viola | 2007/0175952 A1 | 8/2007 | Shelton, IV et al. |
| 2005/0216055 A1 | 9/2005 | Scirica et al. | 2007/0175953 A1 | 8/2007 | Shelton, IV et al. |
| 2005/0230453 A1 | 10/2005 | Viola | 2007/0175954 A1 | 8/2007 | Viola |
| 2005/0263562 A1 | 12/2005 | Shelton, IV et al. | 2007/0175955 A1 | 8/2007 | Shelton, IV et al. |
| 2005/0279804 A1 | 12/2005 | Scirica et al. | 2007/0175956 A1 | 8/2007 | Swayze et al. |
| 2006/0000867 A1 | 1/2006 | Shelton, IV et al. | 2007/0175957 A1 | 8/2007 | Shelton, IV et al. |
| 2006/0000868 A1 | 1/2006 | Shelton, IV et al. | 2007/0175958 A1 | 8/2007 | Shelton, IV et al. |
| 2006/0011699 A1 | 1/2006 | Olson et al. | 2007/0175959 A1 | 8/2007 | Shelton, IV et al. |
| 2006/0016853 A1 | 1/2006 | Racenet | 2007/0175960 A1 | 8/2007 | Shelton, IV et al. |
| 2006/0022014 A1 | 2/2006 | Shelton, IV et al. | 2007/0175961 A1 | 8/2007 | Shelton, IV et al. |
| 2006/0022015 A1 | 2/2006 | Shelton, IV et al. | 2007/0175962 A1 | 8/2007 | Shelton, IV et al. |
| 2006/0025809 A1 | 2/2006 | Shelton, IV | 2007/0175964 A1 | 8/2007 | Shelton, IV et al. |
| 2006/0043147 A1 | 3/2006 | Mastri et al. | 2007/0179528 A1 | 8/2007 | Soltz et al. |
| 2006/0049229 A1 | 3/2006 | Milliman et al. | 2007/0187453 A1 | 8/2007 | Smith et al. |
| 2006/0049230 A1 | 3/2006 | Shelton, IV et al. | 2007/0187454 A1 | 8/2007 | Scirica |
| 2006/0060630 A1 | 3/2006 | Shelton, IV et al. | 2007/0187455 A1 | 8/2007 | Demmy et al. |
| 2006/0081678 A1 | 4/2006 | Ehrenfels et al. | 2007/0194079 A1 | 8/2007 | Hueil et al. |
| 2006/0097026 A1 | 5/2006 | Shelton, IV | 2007/0194080 A1 | 8/2007 | Swayze et al. |
| 2006/0124688 A1 | 6/2006 | Racenet et al. | 2007/0194081 A1 | 8/2007 | Hueil et al. |
| 2006/0124689 A1 | 6/2006 | Arad et al. | 2007/0194082 A1 | 8/2007 | Morgan et al. |
| 2006/0138193 A1 | 6/2006 | Viola et al. | 2007/0221700 A1 | 9/2007 | Ortiz et al. |
| 2006/0138194 A1 | 6/2006 | Viola et al. | 2007/0221701 A1 | 9/2007 | Ortiz et al. |
| 2006/0151567 A1 | 7/2006 | Roy | 2007/0278277 A1 | 12/2007 | Wixey et al. |
| 2006/0151568 A1 | 7/2006 | Weller et al. | 2007/0295780 A1 | 12/2007 | Shelton et al. |
| 2006/0151569 A1 | 7/2006 | Ehrenfels et al. | 2008/0029570 A1 | 2/2008 | Shelton et al. |
| 2006/0175375 A1 | 8/2006 | Shelton, IV et al. | 2008/0029571 A1 | 2/2008 | Shelton et al. |
| 2006/0180634 A1 | 8/2006 | Shelton, IV et al. | 2008/0029572 A1 | 2/2008 | Shelton et al. |
| 2006/0201990 A1 | 9/2006 | Mastri et al. | 2008/0029573 A1 | 2/2008 | Shelton et al. |
| 2006/0201991 A1 | 9/2006 | Mastri et al. | 2008/0029574 A1 | 2/2008 | Shelton et al. |
| 2006/0226195 A1 | 10/2006 | Scirica et al. | 2008/0029575 A1 | 2/2008 | Shelton et al. |
| 2006/0226196 A1 | 10/2006 | Huell et al. | 2008/0029576 A1 | 2/2008 | Shelton et al. |
| 2006/0255090 A1 | 11/2006 | Milliman et al. | 2008/0029577 A1 | 2/2008 | Shelton et al. |
| 2006/0278680 A1 | 12/2006 | Viola et al. | 2008/0048002 A1 | 2/2008 | Smith et al. |
| 2006/0278681 A1 | 12/2006 | Viola et al. | 2008/0078800 A1 | 4/2008 | Hess et al. |
| 2006/0289600 A1 | 12/2006 | Wales et al. | 2008/0078801 A1 | 4/2008 | Shelton et al. |
| 2006/0289602 A1 | 12/2006 | Wales et al. | 2008/0078802 A1 | 4/2008 | Hess et al. |
| 2007/0023477 A1 | 2/2007 | Whitman et al. | 2008/0078803 A1 | 4/2008 | Shelton et al. |
| 2007/0027469 A1 | 2/2007 | Smith et al. | 2008/0078804 A1 | 4/2008 | Shelton et al. |
| 2007/0034669 A1 | 2/2007 | de la Torre et al. | 2008/0078805 A1 | 4/2008 | Omaits et al. |

| | | | |
|---|---|---|---|
| 2008/0078806 A1 | 4/2008 | Omaits et al. |
| 2008/0078807 A1 | 4/2008 | Hess et al. |
| 2008/0078808 A1 | 4/2008 | Hess et al. |
| 2008/0110958 A1 | 5/2008 | McKenna et al. |
| 2008/0110961 A1 | 5/2008 | Voegele et al. |
| 2008/0125812 A1 | 5/2008 | Zubik et al. |
| 2008/0149685 A1 | 6/2008 | Smith et al. |
| 2008/0164296 A1 | 7/2008 | Shelton et al. |
| 2008/0169327 A1 | 7/2008 | Shelton et al. |
| 2008/0169328 A1 | 7/2008 | Shelton |
| 2008/0169329 A1 | 7/2008 | Shelton et al. |
| 2008/0169330 A1 | 7/2008 | Shelton et al. |
| 2008/0169331 A1 | 7/2008 | Shelton et al. |
| 2008/0169332 A1 | 7/2008 | Shelton et al. |
| 2008/0169333 A1 | 7/2008 | Shelton et al. |
| 2008/0210738 A1 | 9/2008 | Shelton et al. |
| 2008/0237296 A1 | 10/2008 | Boudreaux et al. |
| 2008/0237298 A1 | 10/2008 | Schall et al. |
| 2008/0277447 A1 | 11/2008 | Smith et al. |
| 2008/0283570 A1 | 11/2008 | Boyden et al. |
| 2008/0283571 A1 | 11/2008 | Boyden et al. |
| 2008/0283572 A1 | 11/2008 | Boyden et al. |
| 2008/0283574 A1 | 11/2008 | Boyden et al. |
| 2008/0283576 A1 | 11/2008 | Boyden et al. |
| 2008/0283577 A1 | 11/2008 | Boyden et al. |
| 2008/0287987 A1 | 11/2008 | Boyden et al. |
| 2008/0296343 A1 | 12/2008 | Schall et al. |
| 2008/0296344 A1 | 12/2008 | Cropper et al. |
| 2008/0296345 A1 | 12/2008 | Shelton, IV et al. |
| 2008/0296346 A1 | 12/2008 | Shelton, IV et al. |
| 2008/0296347 A1 | 12/2008 | Shelton, IV et al. |
| 2008/0302854 A1 | 12/2008 | Rethy et al. |
| 2008/0308601 A1 | 12/2008 | Timm et al. |
| 2008/0308602 A1 | 12/2008 | Timm et al. |
| 2008/0308603 A1 | 12/2008 | Shelton, IV et al. |
| 2008/0308604 A1 | 12/2008 | Timm et al. |
| 2008/0308606 A1 | 12/2008 | Timm et al. |
| 2008/0308607 A1 | 12/2008 | Timm et al. |
| 2008/0314954 A1 | 12/2008 | Boudreaux |
| 2008/0314955 A1 | 12/2008 | Boudreaux et al. |
| 2008/0314957 A1 | 12/2008 | Boudreaux |
| 2008/0314961 A1 | 12/2008 | Boudreaux et al. |
| 2008/0314962 A1 | 12/2008 | Boudreaux |
| 2009/0001121 A1 | 1/2009 | Hess et al. |
| 2009/0001123 A1 | 1/2009 | Morgan et al. |
| 2009/0001124 A1 | 1/2009 | Hess et al. |
| 2009/0001125 A1 | 1/2009 | Hess et al. |
| 2009/0001126 A1 | 1/2009 | Hess et al. |
| 2009/0001130 A1 | 1/2009 | Hess et al. |
| 2009/0005808 A1 | 1/2009 | Hess et al. |
| 2009/0008424 A1 | 1/2009 | Green |
| 2009/0050671 A1 | 2/2009 | Racenet et al. |
| 2009/0057370 A1 | 3/2009 | Marczyk et al. |
| 2009/0065549 A1 | 3/2009 | Viota |
| 2009/0065550 A1 | 3/2009 | Green et al. |
| 2009/0065551 A1 | 3/2009 | Green et al. |
| 2009/0078738 A1 | 3/2009 | Racenet et al. |
| 2009/0078739 A1 | 3/2009 | Viola |
| 2009/0084826 A1 | 4/2009 | Shah et al. |
| 2009/0090763 A1 | 4/2009 | Zemlok |
| 2009/0090764 A1 | 4/2009 | Viola |
| 2009/0090765 A1 | 4/2009 | Blier et al. |
| 2009/0090766 A1 | 4/2009 | Knodel |
| 2009/0095790 A1 | 4/2009 | Whitman et al. |
| 2009/0101692 A1 | 4/2009 | Whitman |
| 2009/0101694 A1 | 4/2009 | Marczyk |
| 2009/0105535 A1 | 4/2009 | Green |
| 2009/0108048 A1 | 4/2009 | Zemlok et al. |
| 2009/0108049 A1 | 4/2009 | Roy |
| 2009/0114699 A1 | 5/2009 | Viola |
| 2009/0114700 A1 | 5/2009 | Marczyk |
| 2009/0114701 A1 | 5/2009 | Zemlok et al. |
| 2009/0209946 A1 | 8/2009 | Swayze et al. |
| 2009/0209990 A1 | 8/2009 | Yates et al. |
| 2009/0218384 A1 | 9/2009 | Aranyi |
| 2009/0236393 A1 | 9/2009 | Viola |
| 2009/0236395 A1 | 9/2009 | Scirica |
| 2009/0242610 A1 | 10/2009 | Shelton, IV et al. |
| 2009/0242611 A1 | 10/2009 | Hathaway et al. |
| 2009/0255974 A1 | 10/2009 | Viola |
| 2009/0255975 A1 | 10/2009 | Zemlok et al. |
| 2009/0255976 A1 | 10/2009 | Marczyk et al. |
| 2009/0255977 A1 | 10/2009 | Zemlok |
| 2009/0261142 A1 | 10/2009 | Milliman et al. |
| 2009/0261144 A1 | 10/2009 | Sniffin et al. |
| 2009/0261145 A1 | 10/2009 | Heinrich et al. |
| 2009/0266868 A1 | 10/2009 | Wenchell et al. |
| 2009/0272784 A1 | 11/2009 | Farascioni |
| 2009/0272787 A1 | 11/2009 | Scirica |
| 2009/0277946 A1 | 11/2009 | Marczyk |
| 2009/0277947 A1 | 11/2009 | Viola |
| 2009/0277949 A1 | 11/2009 | Viola et al. |
| 2009/0283568 A1 | 11/2009 | Racenet et al. |
| 2009/0289096 A1 | 11/2009 | Shelton, IV et al. |
| 2009/0302090 A1 | 12/2009 | Shah |
| 2009/0302091 A1 | 12/2009 | Shah |
| 2009/0306708 A1 | 12/2009 | Shah |
| 2009/0308907 A1 | 12/2009 | Nalagatla et al. |
| 2009/0308908 A1 | 12/2009 | Green et al. |
| 2009/0308909 A1 | 12/2009 | Nalagatla et al. |
| 2009/0314820 A1 | 12/2009 | Green et al. |
| 2009/0314821 A1 | 12/2009 | Racenet |

FOREIGN PATENT DOCUMENTS

| | | |
|---|---|---|
| DE | 2744824 | 4/1978 |
| DE | 2903159 | 1/1980 |
| DE | 3114135 | 10/1982 |
| DE | 4213426 | 10/1992 |
| DE | 4300307 | 7/1994 |
| EP | 0041022 | 12/1981 |
| EP | 0136950 | 4/1985 |
| EP | 0140552 | 5/1985 |
| EP | 0156774 | 10/1985 |
| EP | 0216532 | 4/1987 |
| EP | 0220029 | 4/1987 |
| EP | 0213817 | 11/1987 |
| EP | 0273468 | 7/1988 |
| EP | 0324166 | 7/1989 |
| EP | 0324635 | 7/1989 |
| EP | 0324637 | 7/1989 |
| EP | 0324638 | 7/1989 |
| EP | 0369324 | 5/1990 |
| EP | 0373762 | 6/1990 |
| EP | 0380025 | 8/1990 |
| EP | 0399701 | 11/1990 |
| EP | 0449394 | 10/1991 |
| EP | 0484677 | 5/1992 |
| EP | 0489436 | 6/1992 |
| EP | 0503662 | 9/1992 |
| EP | 0514139 | 11/1992 |
| EP | 0536903 | 4/1993 |
| EP | 0537572 | 4/1993 |
| EP | 0539762 | 5/1993 |
| EP | 0545029 | 6/1993 |
| EP | 0552050 | 7/1993 |
| EP | 0552423 | 7/1993 |
| EP | 0579038 | 1/1994 |
| EP | 0589306 | 3/1994 |
| EP | 0591946 | 4/1994 |
| EP | 0592243 | 4/1994 |
| EP | 0593920 | 4/1994 |
| EP | 0598202 | 5/1994 |
| EP | 0598579 | 5/1994 |
| EP | 0621006 | 10/1994 |
| EP | 0621009 | 10/1994 |
| EP | 0656188 | 6/1995 |
| EP | 0365153 | 8/1995 |
| EP | 0666057 | 8/1995 |
| EP | 0705571 | 4/1996 |
| EP | 0760230 | 3/1997 |
| EP | 1927319 A | 6/2008 |
| FR | 2542188 | 9/1984 |
| FR | 2660851 | 10/1991 |
| FR | 2681775 | 10/1991 |
| GB | 1352554 | 4/1971 |
| GB | 1452185 | 10/1976 |
| GB | 1555455 | 11/1979 |
| GB | 2048685 | 12/1980 |

| | | |
|---|---|---|
| GB | 2070499 | 9/1981 |
| GB | 2141066 | 12/1984 |
| GB | 2165559 | 4/1986 |
| SU | 728848 | 5/1977 |
| SU | 659146 | 4/1979 |
| SU | 980703 | 12/1982 |
| SU | 990220 | 1/1983 |
| WO | WO 83/02247 | 7/1983 |
| WO | WO 89/10094 | 11/1989 |
| WO | WO 92/10976 | 7/1992 |
| WO | WO 9308754 | 5/1993 |
| WO | WO 9314706 | 8/1993 |
| WO | WO 03/094743 | 11/2003 |
| WO | WO2004/032763 A | 4/2004 |
| WO | WO2005/037329 A | 4/2005 |

OTHER PUBLICATIONS

European Search Report for EP 09251392.8-2310 date of completion is Sep. 18, 2009 (3 pages).

* cited by examiner

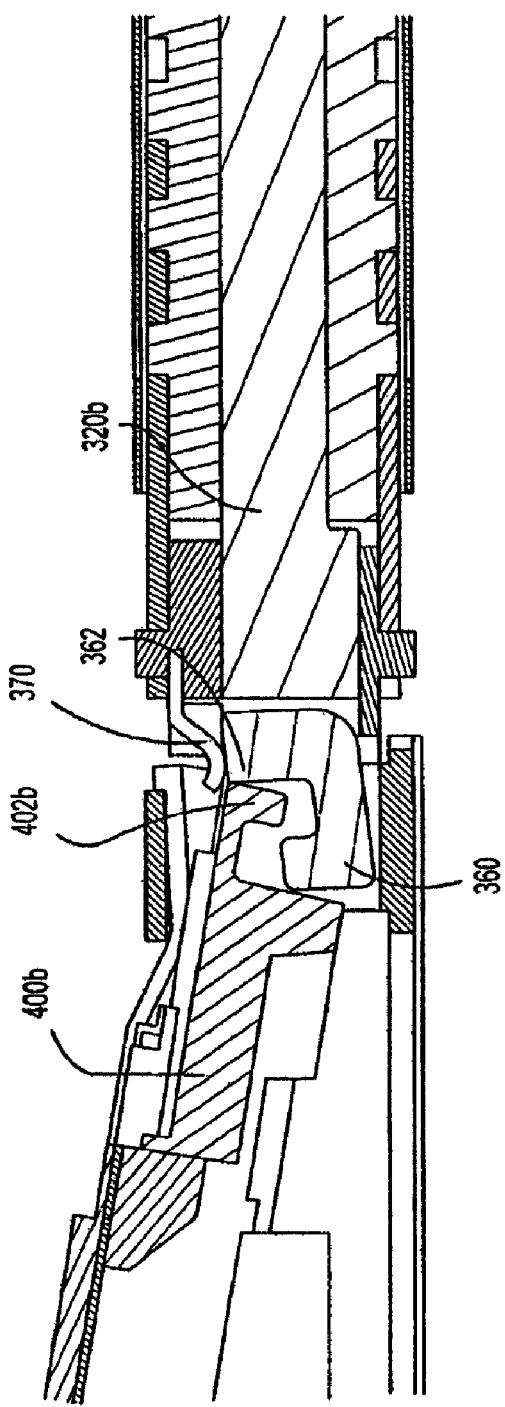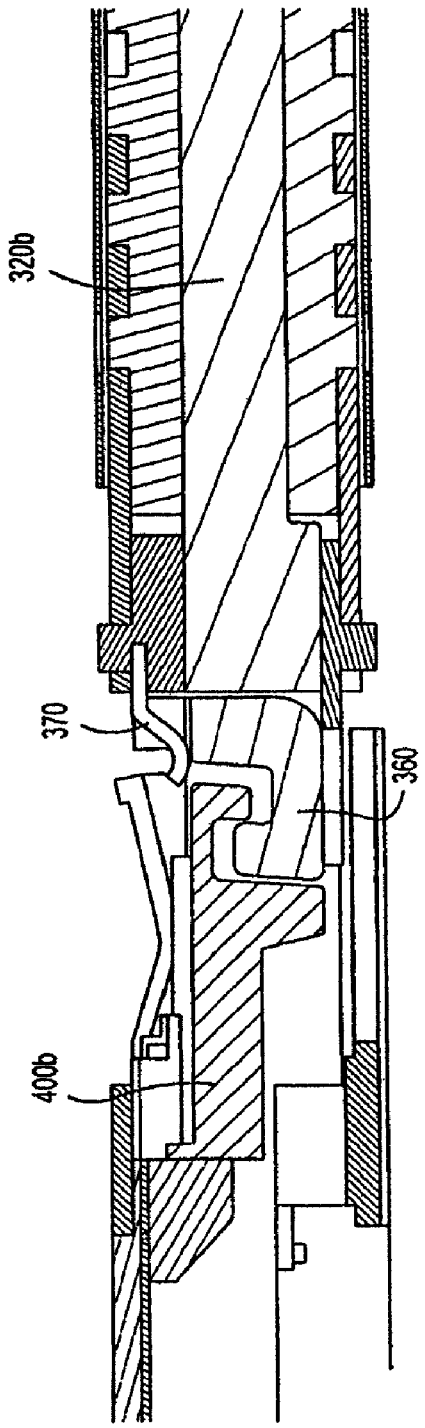

KNIFE/FIRING ROD CONNECTION FOR SURGICAL INSTRUMENT

CROSS-REFERENCE TO RELATED APPLICATIONS

This application is a continuation of U.S. application Ser. No. 12/780,431 filed May 14, 2010, now U.S. Pat. No. 8,074,862, which is a continuation of U.S. application Ser. No. 12/134,351 filed Jun. 6, 2008, now U.S. Pat. No. 7,789,283, and the disclosures of each of the above-identified applications are hereby incorporated by reference in their entirety.

BACKGROUND

1. Technical Field

This present disclosure relates to a surgical instrument having jaws that are movable between open and closed positions, and more particularly to a surgical instrument having a knife bar.

2. Background of Related Art

Surgical devices wherein tissue is first grasped or clamped between opposing jaw structure and then joined by surgical fasteners are well known in the art. In some instruments, a knife is provided to cut the tissue which has been joined by the fasteners. The fasteners are typically in the form of surgical staples but two part polymeric fasteners can also be utilized.

Instruments for this purpose may include two elongated members which are respectively used to capture or clamp tissue. Typically, one of the members carries a staple cartridge that houses a plurality of staples arranged in at least two lateral rows while the other member has an anvil that defines a surface for forming the staple legs as the staples are driven from the staple cartridge. The stapling operation is effected by cam bars that travel longitudinally through the staple cartridge, with the cam bars acting upon staple pushers to sequentially eject the staples from the staple cartridge.

SUMMARY

The present disclosure relates to a surgical instrument including a frame, an elongate portion, a firing rod and an end effector. The elongate portion extends distally from the frame and defines a longitudinal axis. The firing rod is disposed at least partially with the elongate portion and is proximally and distally translatable with respect to the elongate portion. The end effector includes a knife and is disposed at a distal portion of the elongate portion. Distal movement of the firing rod causes a distal end of the firing rod to link with the knife. Proximal movement of the firing rod moves the linked knife proximally to a first predetermined position. The knife is unlinked from the firing rod when the firing rod has been translated proximally to a second predetermined position.

The present disclosure also relates to a surgical instrument including a frame, an elongate portion, a firing rod, a connector, and an end effector. The elongate portion extends distally from the frame and defines a longitudinal axis. The firing rod is disposed at least partially within the elongate portion and is translatable with respect to the elongate portion. The connector is disposed adjacent a distal portion of the firing rod. The end effector is arranged at a distal end of the elongate portion. The end effector includes a first jaw member and a second jaw member. The jaw members are movable with respect to each other between an open position and an approximated position. The end effector includes a first jaw member cartridge having a knife. The connector is engagable with the knife. The connector is configured to link with the knife upon approximation of the jaw members.

DESCRIPTION OF THE DRAWINGS

Various embodiments of the presently disclosed surgical stapling apparatus are disclosed herein with reference to the drawings, wherein:

FIG. 11 illustrates a cross-sectional view of a knife connection in an unlinked position according to an embodiment of the present disclosure;

FIG. 12 illustrates the knife connection of FIG. 11 in a linked position;

DETAILED DESCRIPTION OF EMBODIMENTS

Embodiments of the presently disclosed surgical instrument are described in detail with reference to the drawings wherein like numerals designate identical or corresponding elements in each of the several views. As is common in the art, the term "proximal" refers to that part or component closer to the user or operator, e.g., surgeon or physician, while the term "distal" refers to that part or component farther away from the user.

Figure 1:
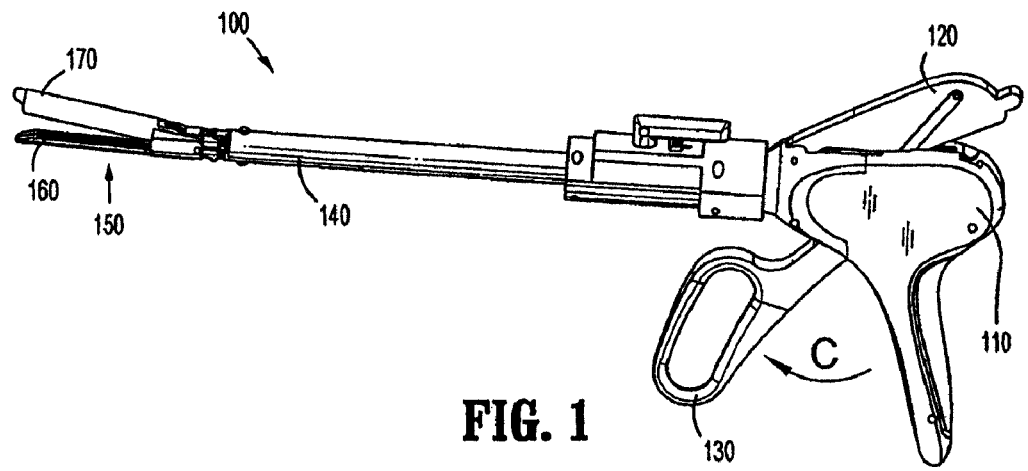
FIG. 1 illustrates a side view of a surgical instrument in accordance with an embodiment of the present disclosure.

Referring to FIG. 1, an embodiment of a surgical instrument 100 of the present disclosure is illustrated. Surgical instrument 100 of this embodiment includes a frame 110, a clamp handle 120, a firing handle 130, an elongate portion 140 and an end effector 150. Elongate portion 140 defines a longitudinal axis "X-X" for surgical instrument 100. Frame 110 is of an overall size and shape convenient for being held in the hand. Clamp handle 120 and firing handle 130 are both pivotally mounted to frame 110 for actuation between open and closed positions.

An example of various aspects of the present disclosure, including the frame, clamp handle, and firing handle, are disclosed in commonly-owned U.S. Pat. No. 5,318,221, the disclosure of which is hereby incorporated by reference herein, in its entirety. Certain aspects of the present disclosure, including actuation of end effector 150, is disclosed in commonly-owned U.S. Pat. No. 6,953,139 to Milliman et al., the entire contents of which are hereby incorporated by reference herein.

As discussed in greater detail below, end effector 150 includes two jaw members—an anvil 160 and a cartridge assembly 170. Anvil 160 and cartridge assembly 170 extend from a distal portion of elongate portion 140. At least one of anvil 160 and cartridge assembly 170 are pivotally movable in relation to the other. Anvil 160 includes a tissue-contacting surface with staple forming depressions thereon (not explicitly shown in the illustrated embodiments). Cartridge assembly 170 includes a plurality of surgical fasteners therein (not explicitly shown in the illustrated embodiments), which are ejectable through tissue and into anvil 160.

A replaceable staple cartridge (or loading unit) may be used with surgical instrument 100 of FIG. 1. The replaceable staple cartridge may house a plurality of staples arranged in at least two lateral rows and may be mountable in a cartridge channel 210 of cartridge assembly 170. Examples of loading units for use with a surgical stapling instrument are disclosed in commonly-owned U.S. Pat. No. 5,752,644 to Bolanos et al., the entire contents of which are hereby incorporated by reference herein.

Figure 2:
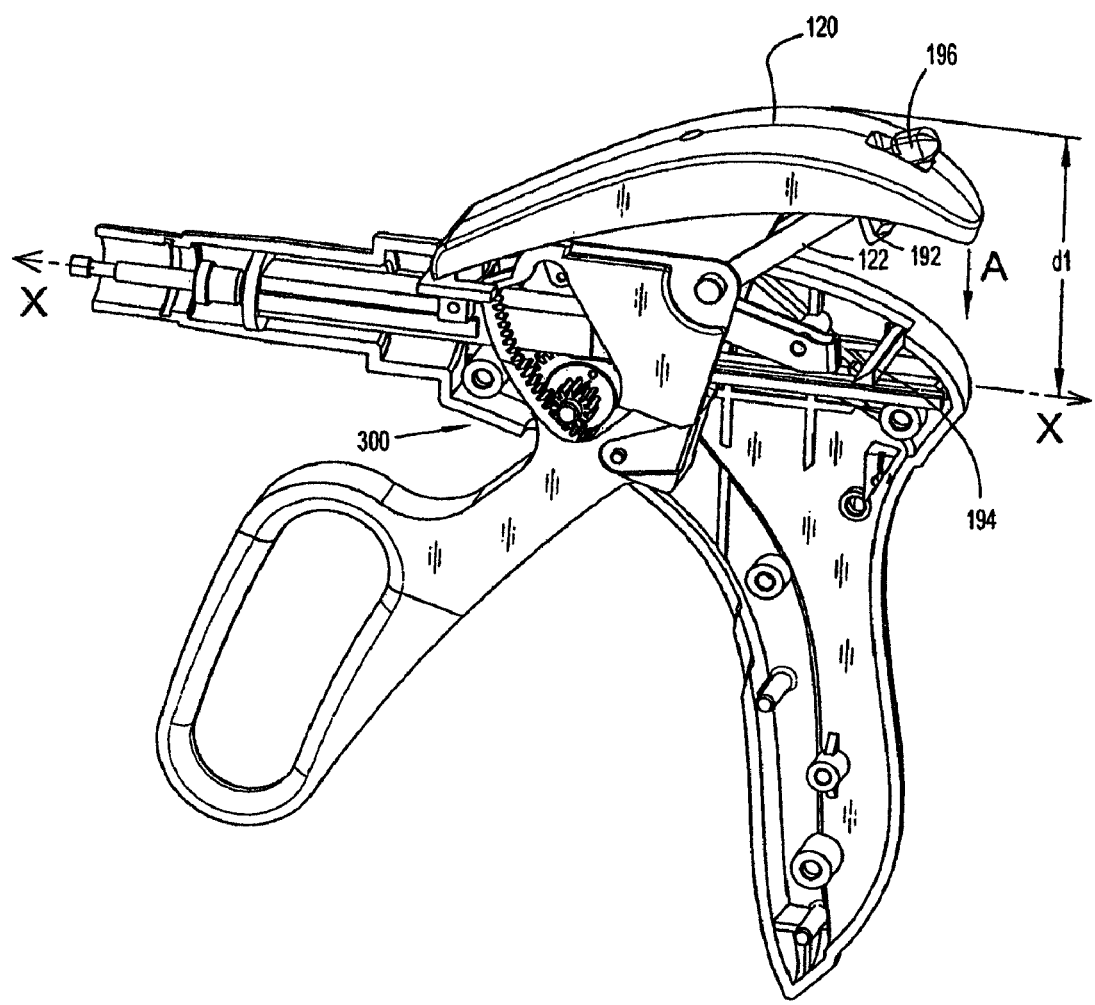
FIG. 2 illustrates a partial cross-sectional view of a frame of the surgical instrument of FIG. 1 showing a clamp handle in an open position.
Figure 3:
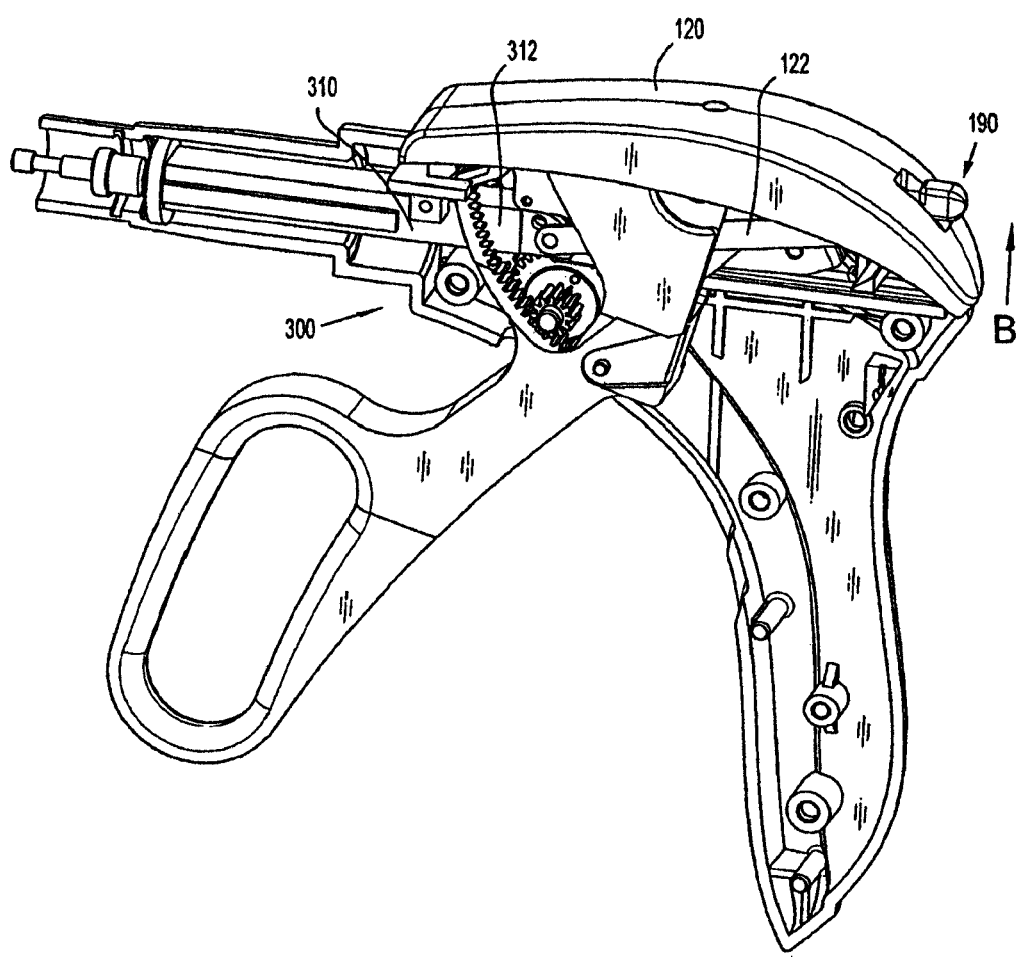
FIG. 3 illustrates a partial cross-sectional view of the frame of FIG. 2 showing the clamp handle in an approximated position.
Figure 4:
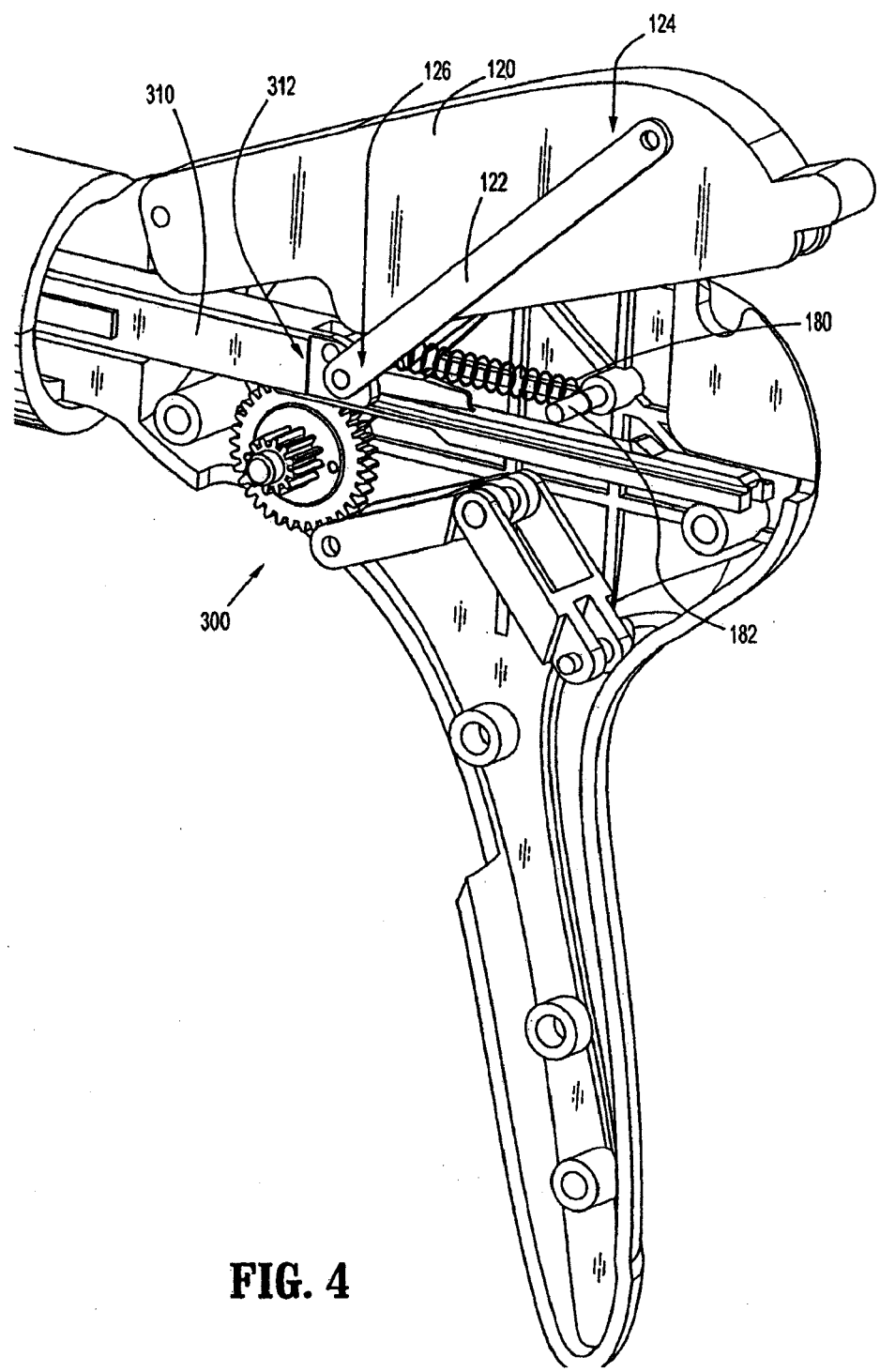
FIG. 4 illustrates a partial cross-sectional view of the frame of FIG. 2 with portions of the frame omitted.

A portion of a drive assembly 300 is illustrated in FIGS. 2-4. Drive assembly 300 of this embodiment includes a drive beam 310. At least a partial actuation of clamp handle 120 is configured to translate drive beam 310 longitudinally to approximate anvil 160 and cartridge assembly 170 with respect to one another. At least a partial actuation of firing handle 130 is configured to translate a firing rod 320 (discussed in greater detail below) longitudinally to eject surgical fasteners (e.g., staples) from cartridge assembly 170 and/or to cut tissue. The firing rod 320 is arranged in the elongate portion 140 and is connected to knife 400 as discussed below. The firing rod 320 is arranged alongside, or concentrically with the drive beam 310.

To clamp tissue, clamp handle 120 is pivoted downward (in the direction of arrow "A" in FIG. 2) towards frame 110. Clamp handle 120 is connected to a handle link 122 such that drive beam 310 moves longitudinally when clamp handle 120 is pivoted closed. This distal longitudinal movement causes a portion of drive beam 310 (e.g., I-beam or actuation portion 330) to contact a camming surface 152 of end effector 150 forcing at least one of anvil 160 and cartridge assembly 170 towards the other. Further details of the clamp handle 120 and drive beam 310 are disclosed in commonly-owned U.S. Pat. No. 5,318,221 to Green et al., the entire contents of which are hereby incorporated by reference herein.

When the surgeon is ready to emplace fasteners and cut tissue, firing handle 130 is actuated, which translates firing rod 320 longitudinally (e.g., distally). An actuation sled may be positioned distally of the distal end of firing rod 320 such that the distal longitudinal movement of firing rod 320 advances the actuation sled in the distal direction. After actuation, firing handle 130 is released and returns to its original position. Further details of firing fasteners and the retraction of firing handle 130 are disclosed in U.S. Pat. No. 5,318,221 to Green et al., previously incorporated by reference.

With continued reference to FIGS. 2-4, further details of clamp handle 120 and internal parts of frame 110 are shown according to an embodiment of the present disclosure. Here, a proximal portion 124 of handle link 122 (e.g., a monolithically formed link) is pivotably engaged with clamp handle 120 (e.g., a proximal portion thereof) and a distal portion 126 of handle link 122 is pivotably engaged with a proximal portion 312 of drive beam 310. A biasing member 180 is illustrated (see FIG. 4), which is configured to bias drive beam 310 proximally (which biases the jaw members in an open position). A proximal portion of biasing member 180 is disposed in mechanical cooperation with frame 110 (e.g., via pin 182) and a distal portion of biasing member 180 is in mechanical cooperation with proximal portion 312 of drive beam 310 (see FIG. 4). As can be appreciated, at least a partial actuation (i.e., movement in the direction of arrow "A") of clamp handle 120 forces distal portion 126 of handle link 122 distally, which causes drive beam 310 to be distally translated against the bias of biasing member 180. As discussed above, distal translation of drive beam 310 causes approximation of the jaw members to clamp tissue therebetween.

With specific reference to FIGS. 2 and 3, surgical instrument 100 of this embodiment includes a latch structure 190 disposed in mechanical cooperation with at least one of frame 110 and clamp handle 120. For example, latch structure 190 may include a first portion 192 disposed on clamp handle 120 and a second portion 194 disposed on frame 110, such that actuation of clamp handle 120 (e.g., a full actuation) causes first portion 192 to engage with second portion 194 to releasably maintain clamp handle 120 in a closed position. Further, a release mechanism 196 may be disposed on a portion of surgical instrument 100 (e.g., clamp handle 120) such that applying pressure to release mechanism 196 (e.g., upward pressure) causes clamp handle 120 to be released from its closed position. That is, activation of release mechanism 196 causes portions 192, 194 of latch mechanism 190 to disengage or unlatch from one another.

In an envisioned embodiment, biasing member 180 is a spring that includes a spring constant which is configured to prevent the jaw members from reaching their approximated position when tissue therebetween exceeds a predetermined thickness. An example when tissue is "too thick" is when the thickness of the tissue between the jaw members would substantially prevent proper emplacement of fasteners therein and/or therethrough.

In a disclosed embodiment, actuation of clamp handle 120 is also configured to provide a user with tactile feedback. For instance, the resistance a user experiences in response to actuating clamp handle 120 may be proportionate to the thickness of the tissue being clamped between the jaw members. Thus, the user is provided with feedback (in the form of resistance) as clamp handle 120 is actuated to approximate the jaw members about tissue therebetween. This feedback may be directly or indirectly proportional to the thickness of the tissue being clamp. It is further envisioned that this amount of force is insufficient to overcome the resistance provided by "too thick" tissue being positioned between the jaw members, thus substantially preventing a user from clamp tissue that is "too thick."

With specific reference to FIG. 2, in its non-actuated or open position, clamp handle 120 (including handle link 122 and various pivot points) is configured to have a relatively low height from the longitudinal axis. Such a relatively small distance provides the overall surgical instrument 100 with a smaller profile, which is generally a desirable feature, as the instrument is less bulky and thus easier to handle. Additionally, it is envisioned that a user can actuate this "low profile" clamp handle 120 with his or her thumb of the same hand that the user uses to actuate movable handle 130 to fire staples, for example. Thus, clamp handle 120 is configured and dimensioned to facilitate one-handed operation of surgical instrument 100.

Figure 5:
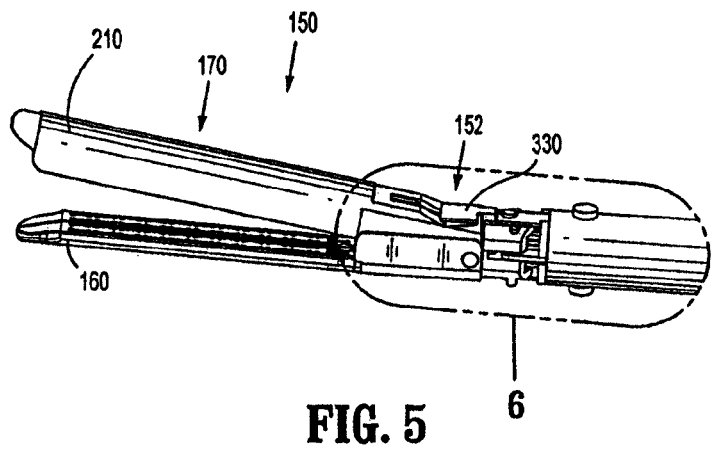
FIG. 5 illustrates a distal portion of the surgical instrument of FIG. 1 showing jaw members in an open position in accordance with an embodiment of the present disclosure.
Figure 6:
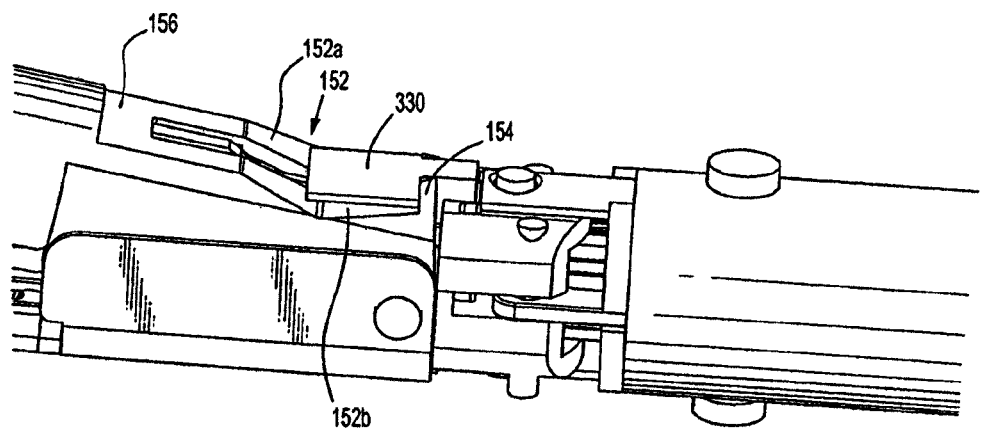
FIG. 6 illustrates an enlarged view of the part of the distal portion of the surgical instrument indicated in FIG. 5.
Figure 7:
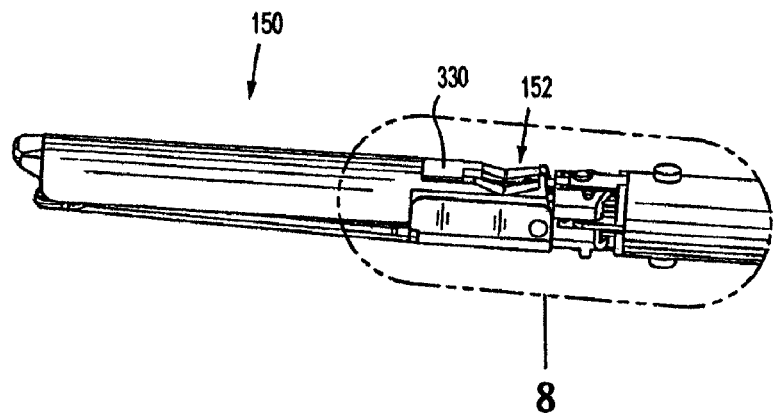
FIG. 7 illustrates a distal portion of the surgical instrument of FIG. 1 showing the jaw members in an approximated position in accordance with an embodiment of the present disclosure.
Figure 8:
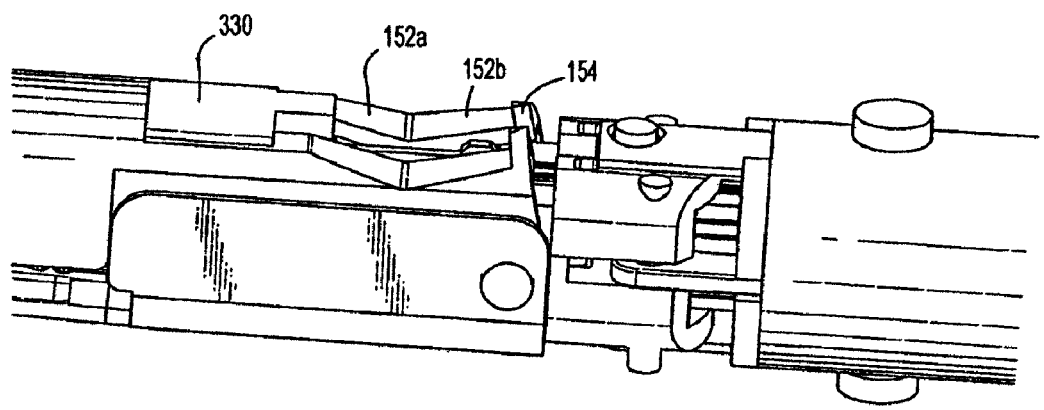
FIG. 8 illustrates an enlarged view of the part of the distal portion of the surgical instrument indicated in FIG. 7.

Referring now to FIGS. 5-8, an embodiment of the present disclosure relating to approximating jaw members is shown. In this embodiment, end effector 150 includes a pair of camming surfaces 152a and 152b. FIGS. 5 and 6 illustrate the jaw members in an open (i.e., non-approximated) position. Here, actuation portion 330 (e.g., an upper horizontal portion of an I-beam) of drive beam 310 is in a first, proximal position. As discussed hereinabove, approximation of clamp handle 120 causes actuation portion 330 of drive beam to translate distally. Upon distal translation of drive beam 310, actuation portion 330 contacts distal camming surface 152a, which causes approximation of the jaw members (e.g., cartridge assembly 170 moves towards a stationary anvil 160). FIGS. 7 and 8 illustrate the result of at least a partial actuation of clamp handle 120, i.e., actuation portion 330 in a distal position and the jaw members in an approximated position.

Once the jaw members are approximated, a user can, for instance, at least partially actuate firing handle 130 to advance the firing rod and eject staples from cartridge assembly 170. The firing handle is desirably biased toward its initial position so that after firing, the firing rod and actuation portion 330 are retracted. Prior to the ejection of staples, the user can raise clamp handle 120 (e.g., in the substantial direction of arrow "B" in FIG. 3) to retract drive beam 310 and cause actuation portion 330 to move proximally and contact proximal camming surface 152b. As actuation portion 330 of drive beam 310 contacts proximal camming surface 152b, the jaw members open with respect to each other (e.g., cartridge assembly 170 moves away from anvil 160). As shown, distal camming surface 152a and proximal caroming surface 152b may be adjacent one other, thus forming a V-like shape.

In the illustrated embodiment, the movable jaw member (e.g., cartridge assembly 170) also includes a lip 154 disposed on a proximal portion thereof. Lip 154 is raised above camming surface 152b and is configured to help prevent actuation portion 330 of drive beam 310 from being translated too far proximally.

Additionally, the movable jaw member is shown having a substantially flat surface 156 (i.e., substantially parallel with the longitudinal axis when the jaw members are approximated) adjacent to and distally of distal camming surface 152a (see FIG. 6). In this configuration, actuation portion 330 of drive beam 310 may continue to translate distally after contacting distal camming surface 152a (and after the jaw members have been at least partially approximated) and may engage surface 156. It is envisioned that engagement between actuation portion 330 and surface 156 may help maintain the jaw members in the approximated position.

Additionally, while not explicitly illustrated herein, it is envisioned that surgical instrument 100 of the present disclosure does not include a clamp handle. In such an embodiment, a partial actuation of firing handle 130 can be used to approximate jaw members and a further, more complete, actuation of firing handle 130 fires staples, for instance. The firing handle, in these embodiments, has a pawl that is biased into engagement with a toothed rack attached to the drive beam. Multiple actuations of the firing handle are used to advance the drive beam. The initial advancement of the drive beam closes the jaw members. With continued actuation of the firing handle, the actuation portion 330 continues to travel distally, firing the staples. The cartridge assembly and anvil include a slot for permitting the actuation portion 330 to travel toward the distal end of the jaw members. The handle assembly disclosed in U.S. Pat. No. 6,953,139 to Milliman et al., the entire contents of which are hereby incorporated by reference herein, may be used. In this embodiment, the actuation portion 330 is connected to the knife member, which pushes the sled 650 to fire the staples.

Referring now to FIGS. 9-17, embodiments of the present disclosure relating to various knife/firing rod connections are shown. In these embodiments, the structure of a portion of firing rod 320 and/or a portion of a knife 400 is configured to enable connection between firing rod 320 and a single-use knife 400, thus enabling a fresh knife 400 to be used for each firing of surgical instrument 100.

Figure 9:
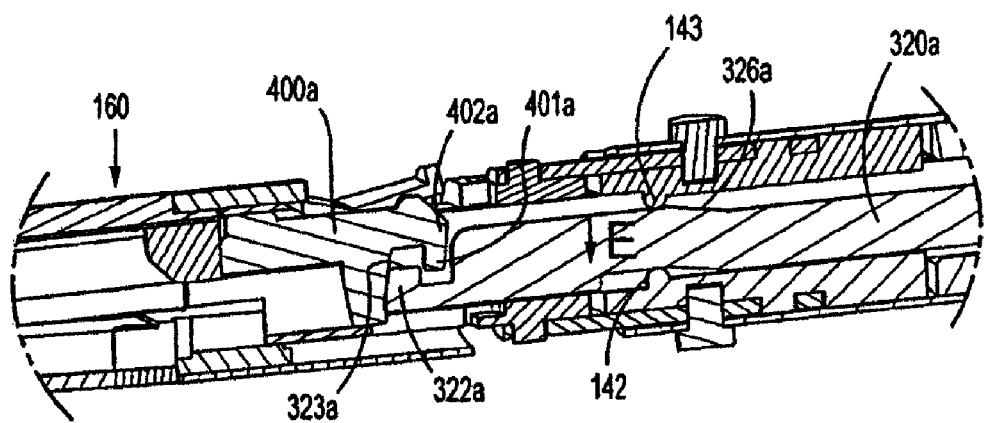
FIG. 9 illustrates an enlarged cross-sectional view of a distal portion of an embodiment of the surgical instrument of the present disclosure showing a knife connection in an unlinked position in accordance with an embodiment of the present disclosure.
Figure 10:
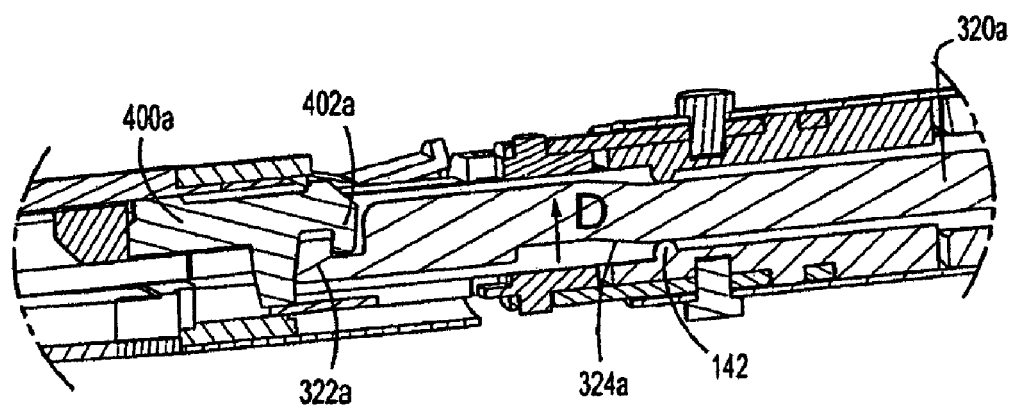
FIG. 10 illustrates the knife connection of FIG. 9 in a linked position.

With particular reference to FIGS. 9 and 10, a first embodiment of a knife/firing rod connection is shown. Specifically, FIG. 9 illustrates firing rod 320a in a first, proximal position where a loading unit, or replaceable cartridge, has been inserted into the cartridge assembly and firing rod 320a and knife 400a are unlinked. FIG. 10 illustrates firing rod 320a in a second, distal position where firing rod 320a and knife 400a are linked. Firing rod 320a and knife 400a of this embodiment are configured such that distal movement of firing rod 320a causes a distal end 322a thereof to link with knife 400a when end effector 150 is engaged with elongate portion 140 of surgical instrument 100. Additionally, proximal movement of firing rod 320a causes knife 400a (which is linked thereto) to move proximally. Further, firing rod 320a and knife 400a are configured to become unlinked with each other when firing rod 320a has been translated proximally to a predetermined position (e.g., corresponding to when firing handle 130 has been substantially fully retracted in the direction of arrow "C" in FIG. 1).

In the unlinked position (i.e., where there is a sufficient distance between a surface 401a of knife 400a and a surface 323a of distal end 322a of firing rod 320a (see FIG. 9)), a user may replace knife 400a with a fresh knife by replacing cartridge assembly 160, for example. While the illustrated embodiments illustrate the jaw members in the approximated position, it is envisioned that a user may remove and/or replace knife 400a when the jaw members are in an open position.

Further details of the interaction between firing rod 320a and knife 400a are described herein with continued reference to FIGS. 9 and 10. As firing rod 320a is advanced distally, at least one projection 142 (e.g., a pair of projections, a radially-disposed projection, etc.) disposed on elongate portion 140 is configured to move at least a portion of firing rod 320a transverse to the longitudinal axis (e.g., in the direction of arrow "D" in FIG. 10). For instance, a projection 143 can contact a ramp 324a of firing rod 320a. As can be appreciated with regard to FIGS. 9 and 10, the combination of the distal movement and the transverse movement causes distal end 322a (e.g., J-shaped) of firing rod 320a to engage (e.g., link) a proximal portion 402a (e.g., J-shaped) of knife 400a. Correspondingly, as firing rod 320a is translated proximally, at least one projection 142 is configured to move at least a portion of firing rod 320a transverse to the longitudinal axis (e.g., in the direction of arrow "E" in FIG. 9). For instance, projection 142 can contact a ramp 326a formed on firing rod 320a. Thus, the combination of the proximal movement and the transverse movement causes distal end 322a of firing rod 320a to disengage (e.g., unlink) proximal portion 402a of knife 400a.

With particular reference to FIGS. 11 and 12, a second embodiment of a knife/firing rod connection is shown. Specifically, FIG. 11 illustrates the jaw members in an open position where knife 400b is not engaged or linked with a connector 360 disposed distally of and adjacent firing rod 320b. FIG. 12 illustrates the jaw members in an approximated position where knife 400b is engaged or linked with connector 360. Connector 360 and knife 400b are configured such that when the jaw members are in the open position, connector 360 and knife 400b are unlinked (FIG. 11), thus allowing the cartridge (including knife 400b) to be removed. When the jaw members are in an approximated position (FIG. 12), a surface of the anvil jaw member contacts the knife 400b, rotating knife 400b so that connector 360 and knife 400b are linked, such that proximal and distal translation of firing rod 320 (and thus connector 360) results in proximal and distal translation of knife 400b, respectively. When the jaw members are approximated, the cartridge cannot be removed from surgical instrument 100, as can be appreciated with reference to FIG. 12.

In the embodiment shown in FIGS. 11 and 12, connector 360 includes a hook-like portion that is configured to engage hook-like portion of knife 400b. Connector 360 is shown having a substantial J-shape, but any suitable shapes can be used for knife 400b and connector 360.

It is envisioned that connector 360 is movable (e.g., pivotable, swivelable, etc.) with respect to the distal end of firing rod 320. For example, when the jaw members are moved towards their open position, a proximal portion 402b of knife 400b may contact an upper portion 362 of connector 360 to pivot/swivel upper portion 362 distally, thus creating enough space (or more space) for knife 400b to be removed from surgical instrument 100. Likewise, when the jaw members are approximated, upper portion 362 of connector 360 may pivot/swivel proximally, thus linking (or further linking) connector 360 with knife 400b, thus not allowing knife 400b to be removed therefrom. Additionally, a flange 370 is shown, which may be configured to help maintain connector 360 in its position and/or to help upper portion 362 of connector 360 move proximally.

Figure 13:
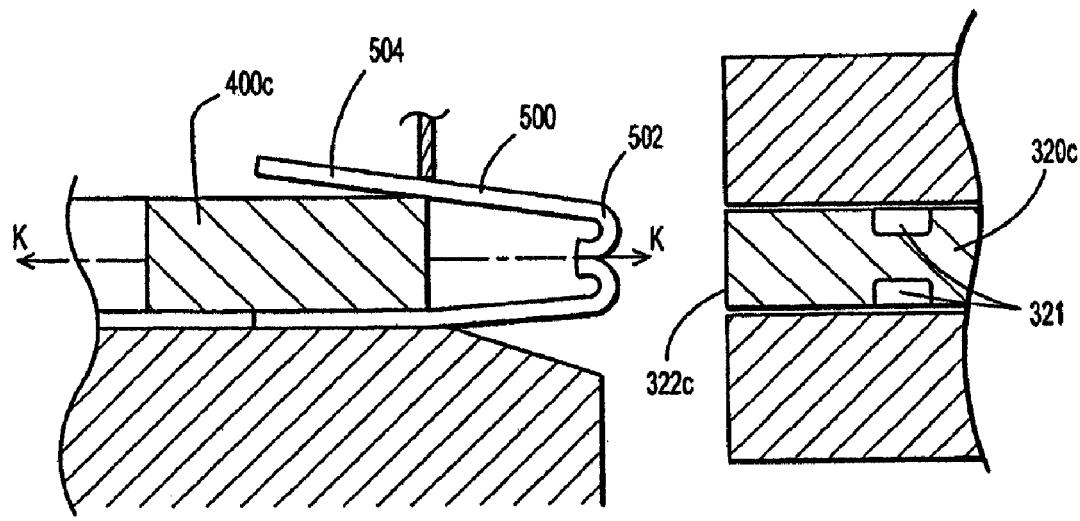
FIG. 13 illustrates a cross-sectional view of a knife connection in an unlinked position according to an embodiment of the present disclosure.
Figure 14:
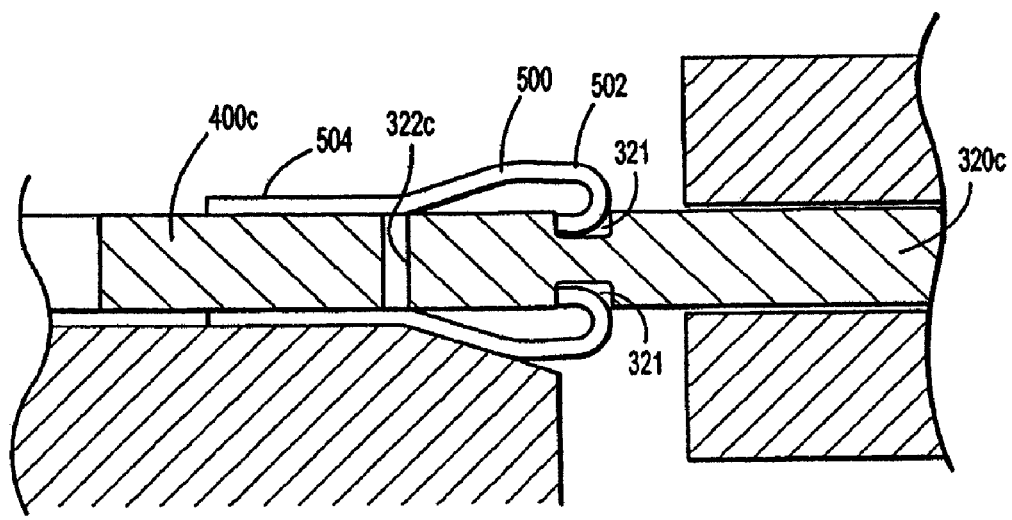
FIG. 14 illustrates the knife connection of FIG. 13 in a linked position.

Another embodiment of a knife/firing rod connection is illustrated in FIGS. 13 and 14. Specifically, FIG. 13 illustrates firing rod 320c in a first, proximal position where firing rod 320c and knife 400c are unlinked. FIG. 14 illustrates firing rod 320c in a second, distal position where firing rod 320c and knife 400c are linked. Firing rod 320c and knife 400c of this embodiment are configured such that distal movement of firing rod 320c causes a distal end 322c thereof to link with knife 400c when end effector 150 is engaged with elongate portion 140 of surgical instrument 100.

More specifically, this embodiment of knife/firing rod connection includes a spring element 500 (e.g., a leaf spring) disposed in mechanical cooperation with knife 400c. The spring element 500 includes a proximal portion 502 and a distal portion 504. The proximal portion 502 (e.g., being substantially J-shaped) of spring element 500 is biased towards a knife axis K-K. Here, distal movement of firing rod 320c urges proximal portion 502 of spring element 500 outwardly (i.e., away from knife axis K-K). The firing rod 320 includes an aperture 321 for receiving the spring element 500. Accordingly, proximal portion 502 of spring element 500 is temporarily secured to firing rod 320c. Thus, continued distal translation of firing rod 320c causes distal translation of knife 400c. Further, proximal translation of firing rod 320c causes proximal translation of knife 400c until firing rod 320c reaches a predetermined location (e.g., corresponding to when firing handle 130 has been substantially fully retracted in the direction of arrow "C" in FIG. 1) where firing rod 320c disengages from spring element 500. Desirably, the shape of the aperture 321 and spring element 500 (or spring elements 500) is such that the spring element 500 is biased outwardly upon removing the cartridge from the device, disconnecting the firing rod 320 from the knife 400.

Figure 15:
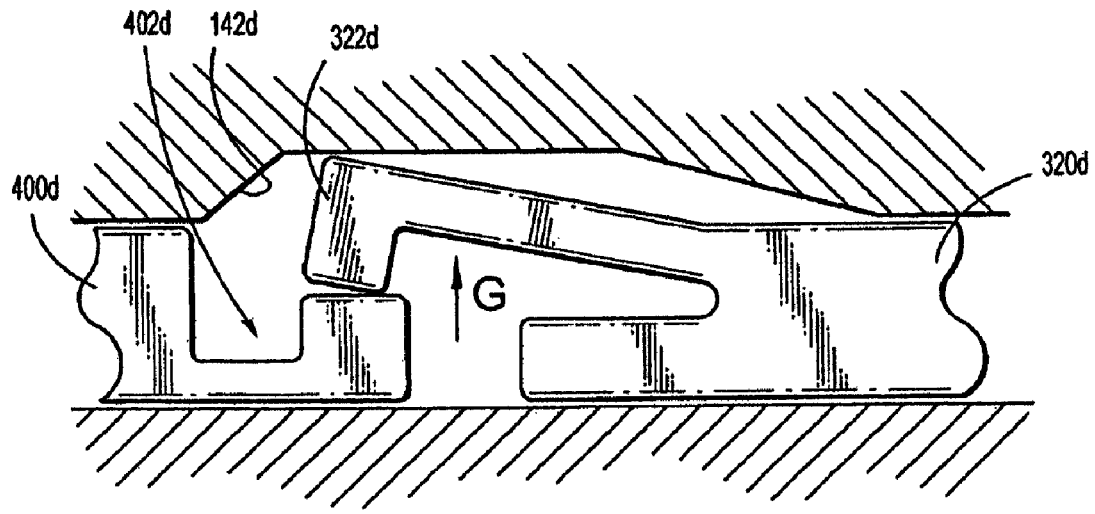
FIG. 15 illustrates a top, cross-sectional view of a knife connection in an unlinked position according to an embodiment of the present disclosure.
Figure 16:
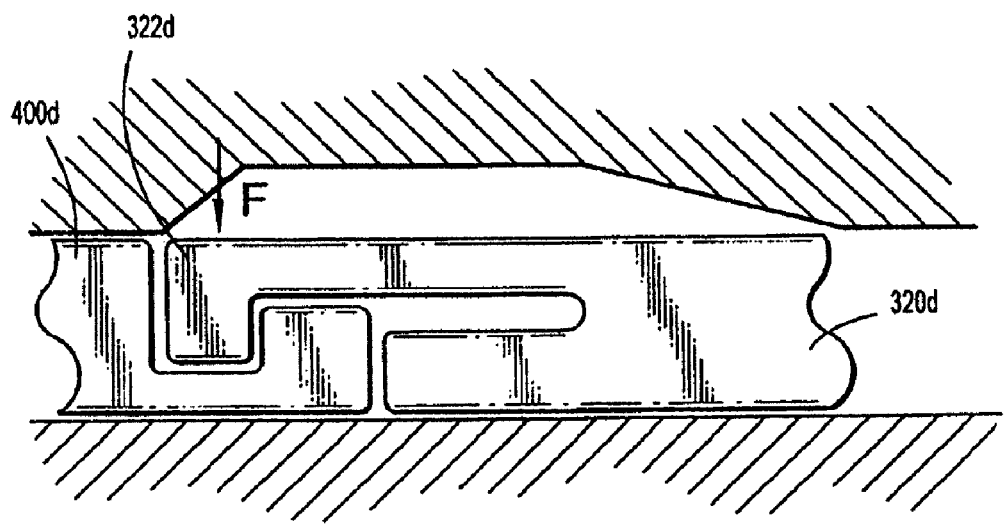
FIG. 16 illustrates the knife connection of FIG. 15 in a linked position.
Figure 17:
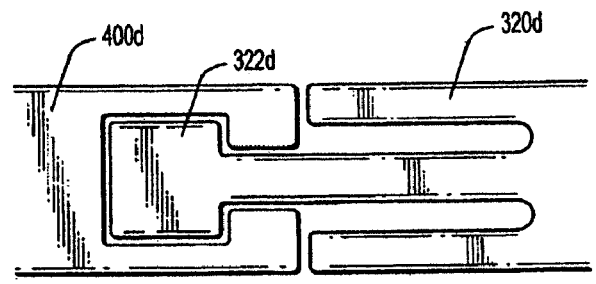
FIG. 17 illustrates a side view of the knife connection of FIG. 16.

With particular reference to FIGS. 15-17, a fourth embodiment of a knife/firing rod connection is shown. Specifically, FIG. 15 illustrates firing rod 320d in a first, proximal position where firing rod 320d and knife 400d are unlinked. FIG. 16 illustrates firing rod 320d in a second, distal position where firing rod 320d and knife 400d are linked. FIG. 17 is a side view of FIG. 16. Firing rod 320d and knife 400d of this embodiment are configured such that distal movement of firing rod 320d causes a distal end 322d thereof to link with knife 400d when end effector 150 is engaged with elongate portion 140 of surgical instrument 100. Additionally, proximal movement of firing rod 320d causes knife 400d (which is linked thereto) to move proximally. Further, firing rod 320d and knife 400d are configured to become unlinked with one another when firing rod 320d has been translated proximally to a predetermined position (e.g., corresponding to when firing handle 130 has been substantially fully retracted in the direction of arrow "C" in FIG. 1). The distal end 322d and receptacle 402d of knife 400d are shaped so that the distal end 322d is biased outwardly upon removing the cartridge from the device, disconnecting the firing rod 320 from the knife 400.

In the unlinked position (FIG. 15), a user may replace knife 400d with a fresh knife by replacing cartridge assembly 160, for example. It is envisioned that the configuration of the end effector and firing rod 320d allows a user to remove and/or replace the cartridge when the jaw members are in an open and/or approximated position.

Further details of the interaction between firing rod 320d and knife 400d are described herein with continued reference to FIGS. 15 and 16. The connection can be formed as the distal end 322d resiliently snaps into the receptacle 402d. Alternatively, as firing rod 320d is advanced distally, a slope 142d disposed on elongate portion 140 is configured to move distal end 322d of firing rod 320d transverse to the longitudinal axis (e.g., in the direction of arrow "F" in FIG. 16) towards a receptacle 402d in knife 400d. Additionally, or alternatively, a slope on the elongate portion can be configured and arranged to pry the distal end 322 away from engagement with the knife. As can be appreciated with regard to FIGS. 15 and 16, the combination of the distal movement and the transverse movement can be used to cause distal end 322d of firing rod 320d to engage receptacle 402d of knife 400d. The combination of the proximal movement and the transverse movement can be used to cause distal end 322d of firing rod 320d to engage receptacle 402d of knife 400d. Similar arrangements can be used for the connection between knife and firing rod shown in FIGS. 13 and 14.

Additionally, it is envisioned that distal end 322d of firing rod 320d is biased away from knife 400d, i.e., in the substantial direction of arrow "G" in FIG. 15. Therefore, as firing rod 320d is translated proximally such that distal end 322d is proximal of slope 142d, distal end 322d moves out of receptacle 402d of knife 400d. Thus, this combination of movement unlinks firing rod 320d and knife 400d.

Figure 18:
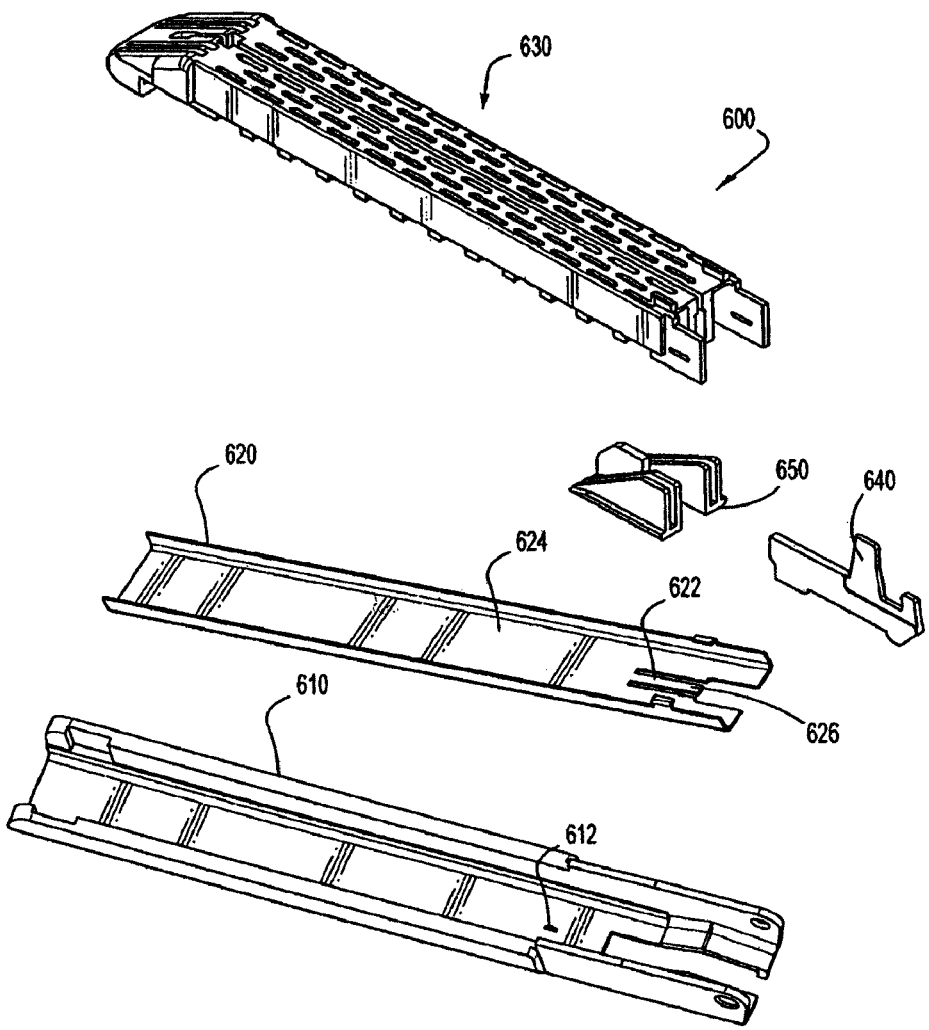
FIG. 18 illustrates an exploded view of a cartridge assembly according to an embodiment of the present disclosure.
Figure 19:
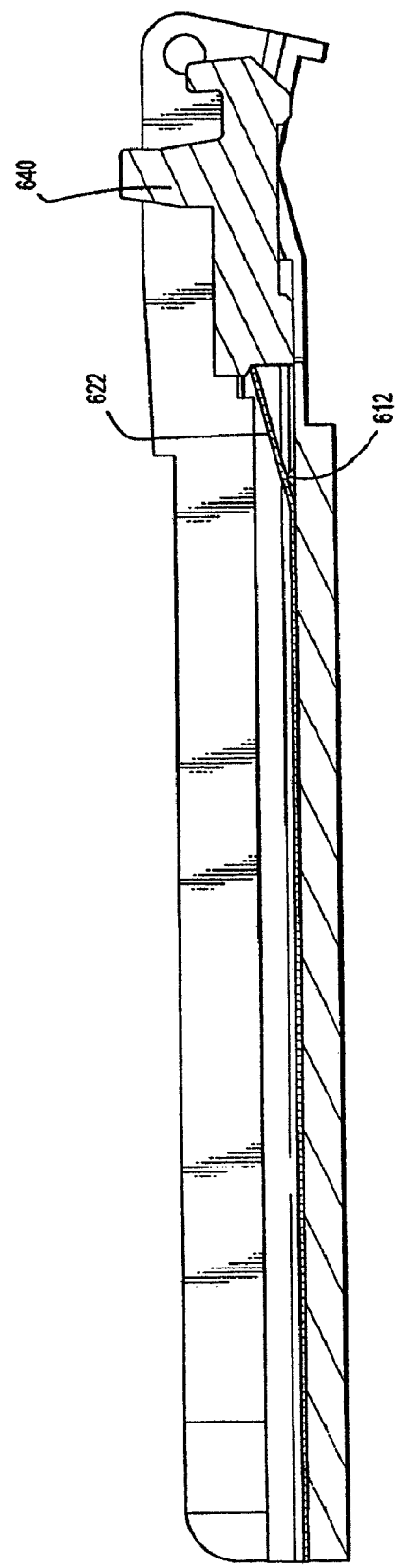
FIG. 19 illustrates a partial, cross-sectional view of the cartridge assembly of FIG. 18.

With reference to FIGS. 18-19, the present disclosure also relates to a cartridge assembly 600 for use with a surgical stapling instrument 100. Cartridge assembly 600 is configured to prevent a user from firing a single-use cartridge that has already been fired. More specifically, cartridge assembly 600 is configured to lock out its knife 640 and prevent re-use of a cartridge, after the cartridge has been fired.

An assembly view of cartridge assembly 600 is shown in FIG. 18. As shown, cartridge assembly 600 includes a channel 610, a cover 620, a staple cartridge 630 and a knife 640. Cover 620 is configured for mechanical engagement (e.g., a snap-fit connection) with channel 610. Staple cartridge 630 is configured for mechanical engagement with cover 620 and knife 640 is configured for translation with respect to cover 620 and cartridge. FIG. 18 also illustrates a sled 650, which is configured for translation with respect to cover 620 (e.g., to eject staples from staple cartridge 630).

As shown, channel 610 includes a protrusion 612 thereon for engagement with a blocking member 622 (e.g., flexible finger) of cover 620. Upon engagement between channel 610 and cover 620, protrusion 612 causes blocking member 622 to move from a first position where blocking member 622 is substantially parallel with a plane defined a surface 624 of cover 620, to a second position where at least a portion of blocking member 622 (e.g., a proximal portion 626) is spaced from the plane of surface 624. In its second position, blocking member 622 is configured to substantially prevent distal translation of knife 640 after knife 640 has been deployed to fire staples, and then translated proximally past a predetermined position (see FIG. 19). It is envisioned that cartridge assembly 600 is configured to allow proximal translation of knife 640 past blocking member 622 when blocking member 622 is in its second position. For example, the blocking member 622 may be formed as a resilient member. In the initial position of the knife, the blocking member 622 is depressed by the knife. After the knife has been advanced, pushing the sled distally to fire staples, the knife is retracted to the position shown in FIG. 19. The blocking member 622 resiliently lifts, engaging a surface on the knife. As can be appreciated, cartridge assembly 600 can be used with various embodiments of surgical stapling instrument 100 described herein.

It will be understood that various modifications can be made to the various embodiments of the present disclosure herein disclosed without departing from the spirit and scope thereof. For example, the surgical stapling instrument of the present disclosure may include a single movable handle for performing all the functions (e.g., approximating the jaw members, firing staples, cutting tissue, opening the jaw members). It is envisioned that the single movable handle can be partially actuated to perform a first function and continued actuation would perform a second function. It is also envisioned that a first complete actuation would perform a first function and a second full actuation would perform a second function.

Further, the disclosed surgical stapling instrument may not include any movable handles; rather, surgical stapling instrument may be powered by means (e.g., battery, electrical, etc.) other than by actuation of a handle or clamp. An example of a powered surgical stapler is disclosed in commonly-owned U.S. patent application Ser. No. 11/786,934, entitled Powered Surgical Instrument, the entire contents of which are hereby incorporated by reference herein. Additionally, the surgical stapling instrument of the present disclosure may also have articulation capabilities, which can move the end effector between a first position where an axis of the end effector is parallel to an axis of the elongate portion, and a second position where the axis of the end effector is at an angle with respect to the axis of the elongate portion. An example of a surgical stapling instrument with an articulatable end effector is disclosed in commonly-owned U.S. patent application Ser. No. 11/544,203, entitled Surgical Instrument with Articulating Tool Assembly, the entire contents of which are hereby incorporated by reference herein. Therefore the above description should not be construed as limiting the disclosure but merely as exemplifications of various embodiments thereof. Those skilled in the art will envision other modifications within the scope and spirit of the present disclosure as defined by the claims appended hereto.

The invention claimed is:

1. A surgical instrument, comprising:
a frame;
an elongate portion extending distally from the frame and defining a longitudinal axis;
a firing rod disposed at least partially within the elongate portion and being movable with respect to the elongate portion from a proximal position to a distal position, the firing rod having an aperture;
an end effector arranged at a distal end of the elongate portion, the end effector including a first jaw member and a second jaw member, the jaw members being movable with respect to each other between an open position and an approximation position, the first jaw member including a knife disposed therein; and
a connector disposed at a proximal portion of the knife, the connector including spring element receivable in the aperture of the firing rod;
wherein distal movement of the firing rod causes the connector to mechanically engage the firing rod.

2. The surgical instrument of claim 1, wherein the connector has a proximal portion that is substantially J-shaped.

3. The surgical instrument of claim 1, wherein distal translation of the firing rod causes distal translation of the knife.

4. The surgical instrument of claim 1, further comprising a movable handle disposed in mechanical cooperation with the frame, and wherein at least a partial actuation of the movement handle effects translation of the firing rod.

5. The surgical instrument of claim 1, wherein the spring element is biased towards a knife axis of the knife.

6. The surgical instrument of claim 1, wherein a proximal portion of the connector is shaped for being received in the aperture.

7. The surgical instrument of claim 1, wherein proximal translation of the firing rod causes proximal translation of the knife.

8. The surgical instrument of claim 1, wherein the first jaw includes a removable staple cartridge.

9. The surgical instrument of claim 8, wherein the shape of the aperture and the connector is such that the connector is biased outwardly upon removing the staple cartridge from the first jaw, disconnecting the connector from the firing rod.

* * * * *